United States Patent
Viola et al.

(10) Patent No.: US 9,463,017 B2
(45) Date of Patent: Oct. 11, 2016

(54) VARIABLE COMPRESSION SURGICAL FASTENER CARTRIDGE

(71) Applicant: Covidien LP, Mansfield, MA (US)

(72) Inventors: Frank J. Viola, Sandy Hook, CT (US); Keith L. Milliman, Bethel, CT (US)

(73) Assignee: Covidien LP, Mansfield, MA (US)

( * ) Notice: Subject to any disclaimer, the term of this patent is extended or adjusted under 35 U.S.C. 154(b) by 706 days.

(21) Appl. No.: 13/871,048

(22) Filed: Apr. 26, 2013

(65) Prior Publication Data

US 2013/0233909 A1 Sep. 12, 2013

Related U.S. Application Data

(63) Continuation of application No. 13/571,311, filed on Aug. 9, 2012, now Pat. No. 8,448,832, which is a continuation of application No. 13/069,602, filed on Mar. 23, 2011, now Pat. No. 8,424,735, which is a (Continued)

(51) Int. Cl.
*A61B 17/068* (2006.01)
*A61B 17/072* (2006.01)
(Continued)

(52) U.S. Cl.
CPC ....... *A61B 17/068* (2013.01); *A61B 17/07207* (2013.01); *A61B 17/105* (2013.01); *A61B 17/0644* (2013.01); *A61B 17/115* (2013.01); *A61B 17/1155* (2013.01); *A61B 2017/07228* (2013.01); *A61B 2017/07235* (2013.01); *A61B 2017/07242* (2013.01);
(Continued)

(58) Field of Classification Search
CPC ............ A61B 17/0644; A61B 17/068; A61B 17/07207; A61B 17/105; A61B 17/115; A61B 17/1155; A61B 2017/07228; A61B 2017/07235; A61B 2017/07242; A61B 2017/320052; Y10S 227/901; Y10S 227/902
USPC ................... 227/175.1–182.1; 411/457, 470; 606/219
See application file for complete search history.

(56) References Cited

U.S. PATENT DOCUMENTS

| 506,861 A | 10/1893 | Prentice |
|---|---|---|
| 1,756,670 A | 4/1930 | Treat |

(Continued)

FOREIGN PATENT DOCUMENTS

| EP | 0 129 442 | 12/1984 |
|---|---|---|
| EP | 0 169 044 | 1/1986 |

(Continued)

OTHER PUBLICATIONS

European Search Report EP06016963.8 dated Mar. 9, 2007.

(Continued)

*Primary Examiner* — Hemant M Desai
*Assistant Examiner* — Valentin Neacsu

(57) ABSTRACT

A surgical fastener applying apparatus having a first jaw and a second jaw. The first jaw includes a cartridge body having plurality of surgical fasteners disposed therein. The plurality of surgical fasteners include a plurality of first surgical fasteners having a first backspan with a first configuration, and a plurality of second surgical fasteners having a second backspan with a second, different configuration such that the plurality of first surgical fasteners apply a first compressive force to tissue upon formation and the plurality of second surgical fasteners apply a second, different compressive force to tissue upon formation.

17 Claims, 22 Drawing Sheets

Related U.S. Application Data continuation of application No. 12/417,685, filed on Apr. 3, 2009, now Pat. No. 7,926,691.

(60) Provisional application No. 61/044,656, filed on Apr. 14, 2008, provisional application No. 61/044,696, filed on Apr. 14, 2008.

(51) Int. Cl.
*A61B 17/10* (2006.01)
*A61B 17/064* (2006.01)
*A61B 17/115* (2006.01)
*A61B 17/32* (2006.01)

(52) U.S. Cl.
CPC .......... *A61B 2017/320052* (2013.01); *Y10S 227/901* (2013.01); *Y10S 227/902* (2013.01)

(56) References Cited

U.S. PATENT DOCUMENTS

| | | |
|---|---|---|
| 3,079,606 A | 3/1963 | Bobrov et al. |
| 3,258,012 A | 6/1966 | Nakayama et al. |
| 3,744,495 A | 7/1973 | Johnson |
| 3,771,526 A | 11/1973 | Rudic |
| 3,800,653 A * | 4/1974 | Barth ............... F16B 15/06 411/474 |
| 3,837,555 A | 9/1974 | Green |
| 4,014,492 A | 3/1977 | Rothfuss |
| 4,278,091 A | 7/1981 | Borzone |
| 4,319,576 A | 3/1982 | Rothfuss |
| 4,340,331 A * | 7/1982 | Savino ............... F16B 15/0015 411/451.2 |
| 4,442,964 A * | 4/1984 | Becht ............... A61B 17/072 227/155 |
| 4,475,679 A | 10/1984 | Fleury, Jr. |
| 4,527,437 A | 7/1985 | Wells |
| 4,531,522 A | 7/1985 | Bedi et al. |
| 4,532,927 A | 8/1985 | Miksza, Jr. |
| 4,548,202 A | 10/1985 | Duncan |
| 4,570,623 A | 2/1986 | Ellison et al. |
| 4,573,469 A | 3/1986 | Golden et al. |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,627,437 A | 12/1986 | Bedi et al. |
| 4,741,336 A | 5/1988 | Failla et al. |
| 4,767,044 A | 8/1988 | Green |
| 4,809,695 A | 3/1989 | Gwathmey et al. |
| 4,848,637 A | 7/1989 | Pruitt |
| 4,881,545 A | 11/1989 | Isaacs et al. |
| 4,930,503 A | 6/1990 | Pruitt |
| 4,941,623 A | 7/1990 | Pruitt |
| 4,978,049 A | 12/1990 | Green |
| 5,027,834 A | 7/1991 | Pruitt |
| 5,108,422 A | 4/1992 | Green et al. |
| 5,180,092 A | 1/1993 | Crainich |
| 5,201,746 A | 4/1993 | Shichman |
| 5,209,756 A | 5/1993 | Seedhom et al. |
| 5,219,353 A | 6/1993 | Garvey, III et al. |
| 5,240,163 A | 8/1993 | Stein et al. |
| 5,282,829 A | 2/1994 | Hermes |
| 5,289,963 A * | 3/1994 | McGarry ............ A61B 17/0684 227/175.1 |
| 5,342,396 A | 8/1994 | Cook |
| 5,350,400 A | 9/1994 | Esposito et al. |
| 5,352,229 A | 10/1994 | Goble et al. |
| 5,425,489 A | 6/1995 | Shichman et al. |
| 5,439,479 A | 8/1995 | Shichman et al. |
| 5,441,193 A | 8/1995 | Gravener |
| 5,452,836 A | 9/1995 | Huitema et al. |
| 5,452,837 A | 9/1995 | Williamson, IV et al. |
| 5,470,010 A | 11/1995 | Rothfuss et al. |
| 5,484,095 A | 1/1996 | Green et al. |
| 5,497,931 A | 3/1996 | Nakamura |
| 5,497,933 A | 3/1996 | DeFonzo et al. |
| 5,501,693 A | 3/1996 | Gravener |
| 5,509,920 A | 4/1996 | Phillips et al. |
| 5,571,116 A | 11/1996 | Bolanos |
| 5,571,285 A | 11/1996 | Chow et al. |
| 5,584,856 A | 12/1996 | Jameel et al. |
| 5,620,452 A | 4/1997 | Yoon |
| 5,634,926 A | 6/1997 | Jobe |
| 5,667,526 A | 9/1997 | Levin |
| 5,667,527 A | 9/1997 | Cook |
| 5,676,674 A | 10/1997 | Bolanos et al. |
| 5,697,542 A | 12/1997 | Knodel et al. |
| 5,709,680 A | 1/1998 | Yates et al. |
| 5,738,474 A | 4/1998 | Blewett |
| 5,741,268 A | 4/1998 | Schutz |
| 5,810,822 A | 9/1998 | Mortier |
| 5,865,361 A | 2/1999 | Milliman et al. |
| 5,871,135 A | 2/1999 | Williamson, IV et al. |
| 5,879,371 A | 3/1999 | Gardiner et al. |
| 5,915,616 A | 6/1999 | Viola et al. |
| 5,961,521 A | 10/1999 | Roger |
| 5,964,394 A | 10/1999 | Robertson |
| 5,976,290 A | 11/1999 | MacDonald et al. |
| 6,083,242 A | 7/2000 | Cook |
| 6,202,914 B1 | 3/2001 | Geiste et al. |
| 6,273,897 B1 | 8/2001 | Dalessandro et al. |
| 6,325,810 B1 | 12/2001 | Hamilton et al. |
| 6,348,054 B1 | 2/2002 | Allen |
| 6,702,826 B2 | 3/2004 | Liddicoat et al. |
| 6,706,057 B1 | 3/2004 | Bidoia et al. |
| 6,786,382 B1 | 9/2004 | Hoffman |
| 6,905,057 B2 | 6/2005 | Swayze et al. |
| 6,915,937 B2 | 7/2005 | Lat et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,001,411 B1 | 2/2006 | Dean |
| 7,044,352 B2 | 5/2006 | Shelton, IV et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,147,140 B2 | 12/2006 | Wukusick et al. |
| 7,303,106 B2 | 12/2007 | Milliman et al. |
| 7,377,928 B2 | 5/2008 | Zubik et al. |
| 7,398,908 B2 | 7/2008 | Holsten et al. |
| 7,407,076 B2 | 8/2008 | Racenet et al. |
| 7,455,676 B2 | 11/2008 | Holsten et al. |
| 7,472,815 B2 | 1/2009 | Shelton et al. |
| 7,500,979 B2 | 3/2009 | Hueil et al. |
| 7,506,791 B2 | 3/2009 | Omaits et al. |
| 7,547,312 B2 | 6/2009 | Bauman et al. |
| 7,604,151 B2 | 10/2009 | Hess et al. |
| 7,641,091 B2 | 1/2010 | Olson et al. |
| 7,669,746 B2 | 3/2010 | Shelton, IV |
| 7,794,475 B2 | 9/2010 | Hess et al. |
| 7,926,691 B2 | 4/2011 | Viola et al. |
| 2001/0044656 A1 | 11/2001 | Williamson et al. |
| 2002/0177850 A1 | 11/2002 | Bremer |
| 2004/0004105 A1 | 1/2004 | Jankowski |
| 2004/0047713 A1* | 3/2004 | Jung ............... F16B 35/041 411/453 |
| 2004/0073222 A1 | 4/2004 | Koseki |
| 2004/0138705 A1 | 7/2004 | Heino et al. |
| 2004/0158267 A1* | 8/2004 | Sancoff ............ A61B 17/0644 606/153 |
| 2004/0232195 A1 | 11/2004 | Shelton et al. |
| 2004/0232199 A1 | 11/2004 | Shelton et al. |
| 2004/0247415 A1 | 12/2004 | Mangone, Jr. |
| 2005/0006430 A1 | 1/2005 | Wales |
| 2005/0006431 A1 | 1/2005 | Shelton et al. |
| 2005/0006434 A1 | 1/2005 | Wales |
| 2005/0023324 A1 | 2/2005 | Doll et al. |
| 2005/0023325 A1 | 2/2005 | Gresham et al. |
| 2005/0070925 A1 | 3/2005 | Shelton, IV et al. |
| 2005/0070958 A1 | 3/2005 | Swayze et al. |

(56) References Cited

U.S. PATENT DOCUMENTS

| | | |
|---|---|---|
| 2005/0139633 A1 | 6/2005 | Wukusick et al. |
| 2005/0173490 A1 | 8/2005 | Shelton, IV |
| 2005/0178813 A1 | 8/2005 | Swayze et al. |
| 2005/0187576 A1 | 8/2005 | Whitman et al. |
| 2005/0263562 A1 | 12/2005 | Shelton, IV et al. |
| 2005/0267530 A1 | 12/2005 | Cummings |
| 2006/0000868 A1 | 1/2006 | Shelton, IV et al. |
| 2006/0015144 A1 | 1/2006 | Burbank et al. |
| 2006/0022014 A1 | 2/2006 | Shelton, IV et al. |
| 2006/0022015 A1 | 2/2006 | Shelton, IV et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton, IV et al. |
| 2006/0025816 A1 | 2/2006 | Shelton, IV |
| 2006/0025817 A1 | 2/2006 | Ortiz et al. |
| 2006/0039779 A1 | 2/2006 | Ring |
| 2006/0049230 A1 | 3/2006 | Shelton, IV et al. |
| 2006/0085030 A1 | 4/2006 | Bettuchi et al. |
| 2006/0097026 A1 | 5/2006 | Shelton, IV |
| 2006/0124688 A1 | 6/2006 | Racenet et al. |
| 2006/0163312 A1 | 7/2006 | Viola et al. |
| 2006/0226196 A1 | 10/2006 | Hueil et al. |
| 2006/0291981 A1 | 12/2006 | Viola et al. |
| 2007/0010838 A1 | 1/2007 | Shelton, IV et al. |
| 2007/0034667 A1 | 2/2007 | Holsten et al. |
| 2007/0045379 A1* | 3/2007 | Shelton ............ A61B 17/07207 227/176.1 |
| 2007/0131732 A1 | 6/2007 | Holsten et al. |
| 2007/0225762 A1* | 9/2007 | LaBombard ....... A61B 17/0057 606/219 |
| 2007/0262116 A1 | 11/2007 | Hueill et al. |
| 2008/0041918 A1 | 2/2008 | Holsten et al. |
| 2008/0078800 A1 | 4/2008 | Hess |
| 2008/0078802 A1 | 4/2008 | Hess |
| 2008/0082124 A1 | 4/2008 | Hess et al. |
| 2009/0255975 A1 | 10/2009 | Zemlok et al. |
| 2009/0255978 A1 | 10/2009 | Viola et al. |
| 2009/0318957 A1 | 12/2009 | Viola |
| 2011/0168760 A1 | 7/2011 | Viola et al. |

FOREIGN PATENT DOCUMENTS

| | | |
|---|---|---|
| EP | 0 588 081 | 3/1994 |
| EP | 0 878 169 | 11/1998 |
| EP | 0 640 315 | 12/1998 |
| EP | 1 090 592 | 4/2001 |
| EP | 1 316 290 | 6/2003 |
| EP | 1 479 346 | 11/2004 |
| EP | 1 607 048 | 12/2005 |
| EP | 1 785 098 | 8/2006 |
| EP | 1 728 473 | 12/2006 |
| EP | 1 754 445 | 2/2007 |
| EP | 1 875 868 | 1/2008 |
| EP | 1 917 918 | 5/2008 |
| EP | 2 095 777 | 9/2009 |
| FR | 2838952 | 10/2003 |
| GB | 2 019 296 | 10/1979 |
| GB | 2 049 296 | 10/1979 |
| GB | 2 029 754 | 3/1980 |
| GB | 2 051 287 | 1/1981 |
| SU | 405234 | 9/1975 |
| SU | 1333319 | 8/1987 |
| SU | 1442191 | 12/1988 |
| SU | 1459659 | 2/1989 |
| WO | WO86/02254 | 4/1986 |
| WO | WO90/05489 | 5/1990 |
| WO | WO96/19146 | 6/1996 |
| WO | WO97/34533 | 9/1997 |
| WO | WO02/30296 | 4/2002 |
| WO | WO03/094743 | 11/2003 |
| WO | WO03/094747 | 11/2003 |
| WO | WO2006/055385 | 5/2006 |
| WO | WO 2008/007377 | 1/2008 |
| WO | WO2008/039250 | 4/2008 |
| WO | WO2008/089050 | 7/2008 |

OTHER PUBLICATIONS

European Search Report EP07 25 4366 dated Nov. 11, 2010.
European Search Report EP08 25 2283 dated Jan. 15, 2009.
European Search Report EP09 25 1067 dated Mar. 17, 2011.
European Search Report EP09 25 1224.3-2310 dated Oct. 8, 2009.
European Search Report EP09251268 dated Sep. 25, 2009.
European Search Report EP09251793.7 dated Nov. 16, 2009.
European Search Report EP10251797 dated Jan. 31, 2011.
European Search Report EP11004299.1269 dated Aug. 12, 2011.
European Search Report EP9251240.9 dated Oct. 19, 2009.
Canadian Office Action dated Mar. 27, 2015 issued in Canadian Application No. 2,673,187.
Japanese Office Action 2009-097516 Apr. 23, 2013.
Japanese Laid-Open Publication No. 07-124166.

* cited by examiner

VARIABLE COMPRESSION SURGICAL FASTENER CARTRIDGE

CROSS-REFERENCE TO RELATED APPLICATIONS

This application is a continuation of U.S. patent application Ser. No. 13/571,311, filed on Aug. 9, 2012, which is a continuation of U.S. patent application Ser. No. 13/069,602, filed on Mar. 23, 2011, now U.S. Pat. No. 8,424,735, which is a continuation of U.S. patent application Ser. No. 12/417,685, filed on Apr. 3, 2009, now U.S. Pat. No. 7,926,691, which claims the benefit of, and priority to, U.S. Provisional Patent Application Ser. Nos. 61/044,656 and 61/044,696, each of which was filed on Apr. 14, 2008, and is now expired, the entire content of each of the applications identified above being incorporated by reference herein.

BACKGROUND

1. Technical Field

The present disclosure relates to surgical fastener applying apparatus. More particularly, the present disclosure relates to surgical fastener applying apparatus that include surgical fasteners that are configured to apply varying compressive forces in tissue.

2. Background of the Related Art

Many varieties of surgical fastener applying apparatus are known in the art, some of which are specifically adapted for use in various surgical procedures including, but not limited to, end-to-end anastomosis, circular end-to-end anastomosis, open gastrointestinal anastomosis, endoscopic gastrointestinal anastomosis, and transverse anastomosis. Suitable examples of apparatus which may be used during the course of these procedures can be seen in U.S. Pat. Nos. 5,915,616; 6,202,914; 5,865,361; and 5,964,394.

In general, a surgical fastener applying apparatus will include an anvil that is approximated relative to a surgical fastener cartridge during use or a fastener cartridge that is approximated relative to an anvil. The anvil includes depressions that are aligned with, and/or are in registration with slots defined in the surgical fastener cartridge, through which the fasteners will emerge. To effectuate formation, the fasteners emerge from the surgical fastener cartridge and are driven against the anvil. The surgical fastener cartridge typically has one or more rows of fasteners disposed laterally outward of a channel or knife slot that is configured to accommodate a knife, or other such cutting element, such that tissue can be simultaneously severed and joined together. Depending upon the particular surgical fastener applying apparatus, the rows of fasteners may be arranged in a linear, non-linear, e.g. circular, semi-circular, arcuate, or other configuration.

Various types of surgical fasteners are well known in the art including, but not limited to, unitary fasteners and two-part fasteners. Unitary fasteners generally include a pair of legs that are adapted to penetrate tissue and connected by a backspan from which they extend. In use, subsequent to formation, certain types of unitary fasteners have a "B" shaped configuration. Typically, the two-part fastener includes legs that are barbed and connected by a backspan. The legs are engaged and locked into a separate retainer piece that is usually located in the anvil. In use, the two-part fastener is pressed into the tissue so that the barbs penetrate the tissue and emerge from the other side where they are then locked into the retainer piece.

During each of the aforementioned surgical procedures, the tissue is initially gripped or clamped between the cartridge and anvil such that individual fasteners can be ejected from the cartridge, through the slots, and forced through the gripped tissue. Thereafter, the fasteners are formed by driving them into the depressions formed on the anvil.

A common concern in each of the procedures mentioned above is hemostasis, or the rate at which bleeding of the target tissue is stopped. It is commonly known that by increasing the amount of pressure applied to a wound, the flow of blood can be limited, thereby decreasing the time necessary to achieve hemostasis. To this end, conventional surgical fastener applying apparatus generally apply two or more rows of fasteners about the cut-line to compress the surrounding tissue in an effort to stop any bleeding and to join the cut tissue together. Each of the fasteners will generally apply a compressive force to the tissue sufficient to effectuate hemostasis. However, applying too much pressure can result in a needless reduction in blood flow to the tissue surrounding the cut-line, resulting in an elevated level of necrosis, a slower rate of healing, and/or a greater recovery period.

Consequently, it would be advantageous to provide a surgical fastener applying apparatus capable of limiting the flow of blood in the tissue immediately adjacent the cut-line to effectuate hemostasis and wound closure, while maximizing blood flow in the surrounding tissue to facilitate healing.

Additionally, when tissue is clamped and compressed between the anvil and the surgical fastener cartridge, some of the fluid of the tissue is squeezed out so the tissue is compressed further at the center portions of the cartridge and anvil than at the lateral edges, thereby leaving thicker tissue at the edges. It would therefore be advantageous to provide surgical fasteners which could better accommodate these resulting different tissue thicknesses.

SUMMARY

In one aspect of the present disclosure, a surgical fastener applying apparatus is disclosed having a first jaw and a second jaw. The first jaw includes a cartridge body having plurality of surgical fasteners disposed therein. The plurality of surgical fasteners include a plurality of first surgical fasteners having a first backspan with a first configuration, and a plurality of second surgical fasteners having a second backspan with a second, different configuration such that the plurality of first surgical fasteners apply a first compressive force to tissue upon formation and the plurality of second surgical fasteners apply a second, different compressive force to tissue upon formation.

In one embodiment, the first surgical fasteners are arranged in a first row and the second surgical fasteners are arranged in a second row laterally outward of the first row wherein the first and second backspans are configured and dimensioned such that the first compressive force is greater than the second compressive force, whereby blood flow through tissue surrounding the plurality first surgical fasteners after formation is less than blood flow through tissue surrounding the plurality of second surgical fasteners after formation.

In some embodiments, each surgical fastener in the plurality of surgical fasteners defines a substantially equivalent overall height when formed in the tissue.

In one embodiment, the first configuration of the first backspan of the plurality of first surgical fasteners include a twisted configuration defining a first height, and the second configuration of the second backspan of the plurality of second surgical fasteners include a backspan having a twisted configuration defining a second height less than the first height.

The cartridge body may include a channel that is configured to accommodate a cutting member for the creation of a cut-line in the patient's tissue. When the plurality of surgical fasteners are arranged within the cartridge body, the plurality of first surgical fasteners may be arranged to define a pair of first rows disposed laterally outwardly of the channel, and the second surgical fasteners may be arranged to define a pair of second rows disposed laterally outwardly of the pair of first rows.

In some embodiments, the plurality of surgical fasteners loaded into the cartridge body may further include a plurality of third surgical fasteners each with a third backspan having a third configuration that is different than at least one, and preferably both, of the respective first and second configurations of the first and second backspans. The third fasteners can be arranged in a third pair of rows laterally outward of the pair of second rows.

The third fasteners may be configured and dimensioned to apply a third compressive force to the tissue upon formation of the plurality of third surgical fasteners that is different than at least one, and preferably both, of the respective first and second compressive forces applied to the tissue by the first and second backspans upon formation of the plurality of first surgical fasteners and the plurality of second surgical fasteners. Preferably, the first compressive force is greater than the third compressive force, whereby blood flow through the tissue surrounding the plurality of first surgical fasteners after formation is less than blood flow through the tissue surrounding the plurality of third surgical fasteners after formation. Preferably, the third backspan is configured and dimensioned such that the second compressive force is greater than the third compressive force, whereby blood flow through the tissue surrounding the plurality of second surgical fasteners after formation is less than blood flow through the tissue surrounding the plurality of third surgical fasteners after formation.

In one embodiment, the third backspan of the plurality of third surgical fasteners may be substantially linear in configuration. Alternatively, the third backspan may have a twisted configuration which is preferably similar to the twisted backspan of the second fasteners, except defining a third height that is less than the second height defined by the second backspan of the plurality of second surgical fasteners or alternatively have an inwardly directed curve defining a third height less than second height.

In an alternative embodiment, the plurality of first surgical fasteners include first legs extending from the first backspan and terminating in penetrating ends, as well as at least one curve that is formed in the first backspan, wherein the at least one curve extends towards the penetrating ends and is dimensioned to define a first height. Additionally, or alternatively, the plurality of second surgical fasteners may include second legs extending from the second backspan and terminating in penetrating ends, as well as at least one curve that is formed in the second backspan, wherein the at least one curve extends towards the penetrating ends and is dimensioned to define a second height that is less than the first height.

In another aspect of the present disclosure, a surgical fastener cartridge is provided including a plurality of surgical fasteners disposed therein. The plurality of surgical fasteners include a plurality of first surgical fasteners arranged in a first row and having a first backspan with a first configuration, and a plurality of second surgical fasteners arranged in a second row and having a second backspan with a second configuration. The first backspan has a first height and the second backspan has a second height, the first height being less than the second height.

In one embodiment, the first and second backspans have a twisted configuration and the first fastener applies a first compressive force to tissue upon formation, and the second surgical fasteners apply a second, lesser compressive force to tissue upon formation.

In one embodiment, the first surgical fasteners include first legs extending from the first backspan and terminating in penetrating ends and the second surgical fasteners include second legs extending from the second backspan and terminating in penetrating ends, wherein the first backspan includes at least one portion curving inwardly toward the penetrating ends of the first legs to form a humped configuration and dimensioned to define a first height, and the second backspan includes at least one portion curving inwardly toward the penetrating ends of the second legs to form a humped configuration and dimensioned to define a second height different from the first height.

In preferred embodiments, the plurality of first fasteners define a pair of first rows and the plurality of second surgical fasteners define a pair of second rows disposed further from the central longitudinal axis of the cartridge than the pair of first rows.

The cartridge may include a plurality of third surgical fasteners having a third backspan with a third configuration such that the plurality of third surgical fasteners apply a third compressive force to the tissue upon formation that is different from at least one of the first compressive force and the second compressive force respectively applied to the tissue by the plurality of first surgical fasteners and the plurality of second surgical fasteners upon formation, the third fasteners being disposed further from the central longitudinal axis of the pair of first rows.

These and other features of the surgical fastener applying apparatus, surgical fastener cartridge, and surgical fasteners disclosed herein will become more readily apparent to those skilled in the art through reference to the detailed description of various embodiments of the present disclosure that follows.

BRIEF DESCRIPTION OF THE DRAWINGS

Various embodiments of the present disclosure are described herein, with references to the drawings, wherein.

DETAILED DESCRIPTION OF EXEMPLARY EMBODIMENTS

Figure 1:
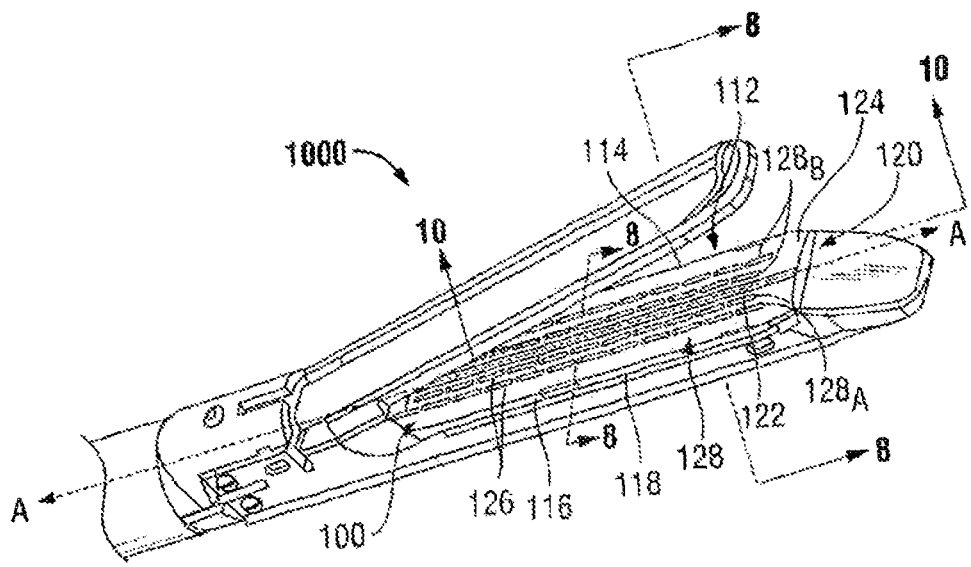
FIG. 1 is a top, perspective view of a distal end portion of a surgical fastener applying apparatus including a surgical fastener cartridge in accordance with one embodiment of the present disclosure.

Various exemplary embodiments of the presently disclosed surgical fastener applying apparatus, surgical fastener cartridge, and surgical fasteners will now be described in detail with reference to the drawings wherein like references characters identify similar or identical elements. In the drawings, and in the description which follows, the term "proximal" will refer to the end of the surgical fastener applying apparatus that is closer to the clinician during use, while the term "distal" will refer to the end that is further from the clinician, as is traditional and conventional in the art. In addition, the term "surgical fastener" should be understood to include any substantially rigid structure that is suitable for the intended purpose of joining tissue together, including but not being limited to surgical staples, clips, and the like.

FIG. 1 illustrates a distal end portion of an exemplary surgical fastener applying apparatus 1000 including a surgical fastener cartridge 100 in accordance with the principles of the present disclosure. The surgical fastener cartridge 100 extends along a longitudinal axis "A-A," and includes a cartridge body 112 with a pair of side walls 114, 116, a bottom wall 118, and a top wall 120. The top wall 120 includes a knife slot or channel 122 that is configured to accommodate longitudinal movement of a knife member 123 (FIG. 16) or other cutting element such that tissue may be severed along a cut-line. The top wall 120 further includes a tissue engaging surface 124 for maintaining the position of the tissue to be cut, and a plurality of fastener retention slots 126 that are arranged into a plurality of rows 128 that extend along the length (longitudinal axis) of the surgical fastener cartridge 100. As shown in FIG. 1, the fastener retention slots 126 are arranged into a pair of first (inner) rows $128_A$ that are spaced laterally outward from the channel or knife slot 122, on opposite sides thereof, and a pair of second (outer) rows $128_B$ that are spaced laterally outward from the pair of first rows $128_A$, again on opposite sides of the slot 122. While the surgical fastener cartridge 100 is depicted as including pairs of first and second rows $128_A$, $128_B$, respectively, additional rows of fastener retention slots 126 (and fasteners) may be included in alternative embodiments of the surgical fastener cartridge 100, as discussed below. In various embodiments of the present disclosure, it is envisioned that the surgical fastener cartridge 100 may be removable, or replaceable, with another loaded surgical fastener cartridge.

Each of the fastener retention slots 126 is configured to receive one of a plurality of surgical fasteners, e.g., the surgical fasteners and pushers 129 (FIG. 8) such that the surgical fasteners are deployed in rows, e.g. inner and outer rows in the embodiment shown in FIG. 1, on opposite sides of the cut-line created in the tissue during the surgical fastening procedure.

Further details regarding the fastener cartridge 100 may be obtained through reference to U.S. Pat. No. 7,070,083, the entire contents of which are incorporated herein by reference.

Figure 2:
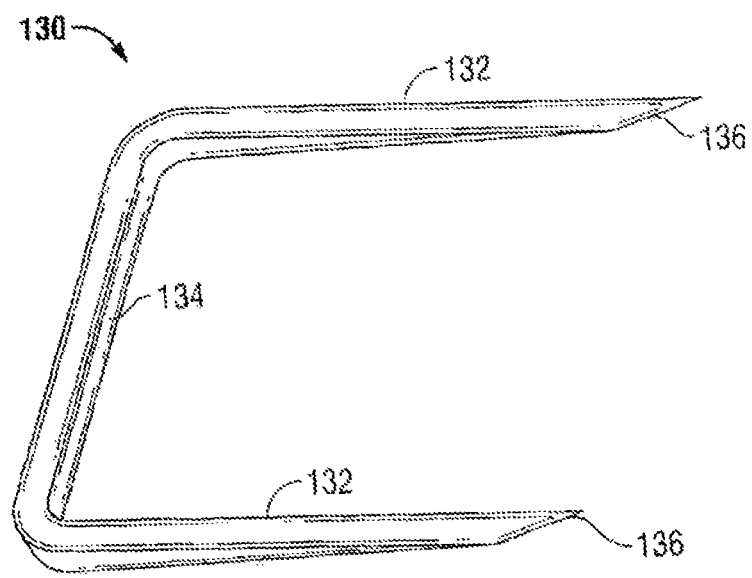
FIG. 2 is a side, perspective view of one embodiment of a surgical fastener, including a substantially linear backspan and shown prior to formation, for use with the surgical fastener cartridge seen in FIG. 1.
Figure 3:
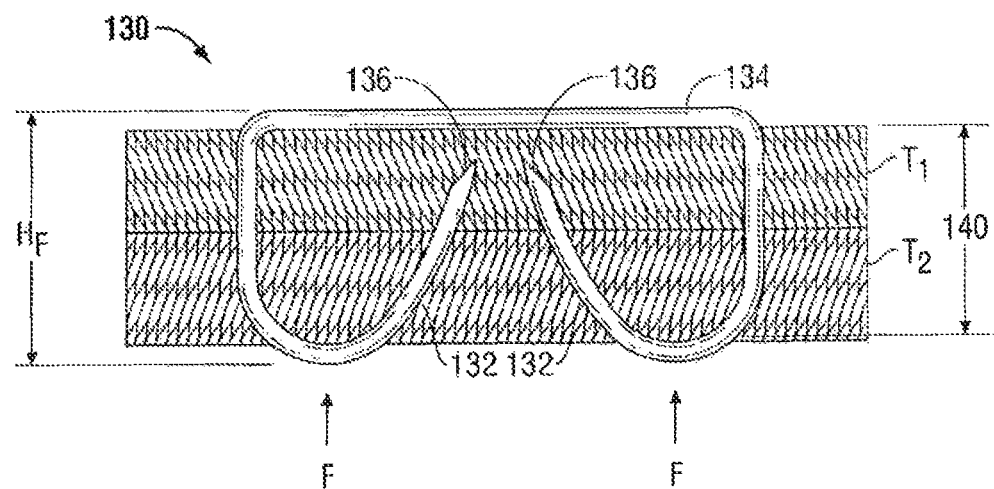
FIG. 3 is a cross-sectional view of the surgical fastener shown in FIG. 2 subsequent to formation within adjacent tissue segments.

Referring now to FIGS. 2 and 3 as well, the surgical fastener cartridge 100 is loaded with one or more varieties of surgical fastener, one of which may be the surgical fastener 130. The surgical fastener 130 includes two legs 132 extending from a backspan 134 extending therebetween. The thickness of the backspan 134 and the legs 132 can be varied such that the surgical fastener 130 may be used to fasten adjacent tissue segments "$T_1$," "$T_2$" of any thickness.

The legs 132 and the backspan 134 may define a cross-section having any suitable geometric configuration, including but not being limited to rectangular, oval, square, triangular, trapezoidal, etc. The legs 132 and the backspan 134 may exhibit the same geometrical configuration such that the cross-sectional configuration of the surgical fastener 130 is substantially uniform, as shown in FIGS. 2, 3, or alternatively, the legs 132 and the backspan 134 may exhibit different geometrical configurations, e.g., the legs 132 may exhibit a rectangular cross-sectional configuration whereas the backspan 134 may exhibit an oval cross-sectional configuration.

Prior to formation of the surgical fastener 130, the legs 132 extend from the backspan 134 such that they are substantially parallel. Alternatively, the legs 132 may converge or diverge from the backspan forming an acute or obtuse angle with the backspan. Each of the legs 132 terminates in a penetrating end 136 that is configured to penetrate tissue, e.g., tissue segments "$T_1$," "$T_2$" (FIG. 3). The penetrating ends 136 of legs 132 can be tapered to facilitate the penetration of the tissue segments "$T_1$," "$T_2$," or alternatively, the penetrating ends 136 may not include a taper. In various embodiments of the surgical fastener 130, it is also envisioned that the penetrating ends 136 may alternatively define either conical or flat surfaces, as described in co-pending U.S. application Ser. No. 11/444, 761, filed Apr. 13, 2003, the entire contents of which are incorporated herein by reference. The surgical fastener 130 may also be configured as a directionally biased staple, such as that described in commonly owned U.S. Pat. No. 7,398, 907, the entire contents of which are incorporated herein by reference.

In the embodiment of the surgical fastener 130 illustrated in FIGS. 2 and 3, the backspan 134 is substantially linear in configuration. When formed within tissue, e.g., within the tissue segments "$T_1$," "$T_2$" (FIG. 3), the legs 132 of the surgical fastener 130 cooperate with the backspan 134 to maintain adjacent tissue segments "$T_1$," "$T_2$" in approximation and apply a compressive force "F" thereto. The compressive force "F" applies pressure to the tissue segments "$T_1$," "$T_2$," thereby restricting the flow of blood through the tissue surrounding the surgical fastener 130 and facilitating hemostasis. The linear configuration of the backspan 134 limits the amount of pressure that can be applied to the tissue segments "$T_1$," "$T_2$," however, such that the flow of blood through the tissue is not completely restricted. When formed, the surgical fastener 130 forms a substantially "B" shaped configuration and defines an overall height "$H_F$," measured from the backspan 134 to the outermost curve of the formed legs 132.

Figure 4:
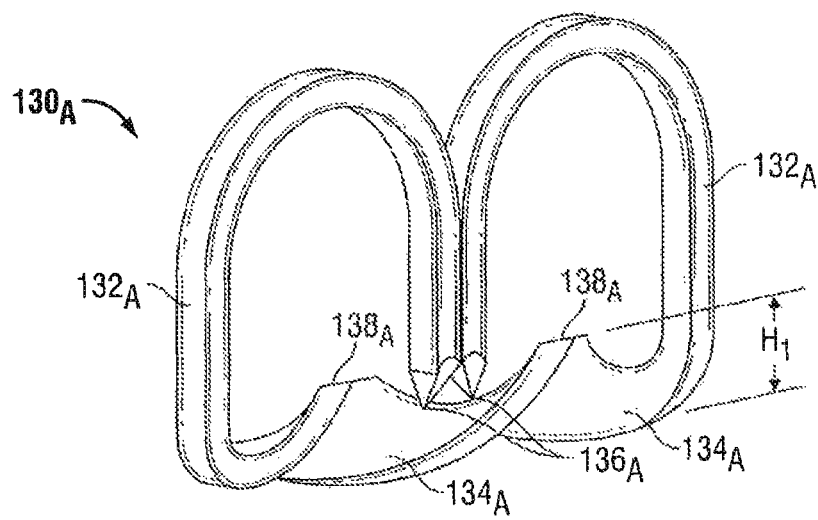
FIG. 4 is a side, perspective view of an alternative embodiment of the surgical fastener shown in FIG. 2 including a twisted backspan with a plurality of protrusions defining a first height.
Figure 5:
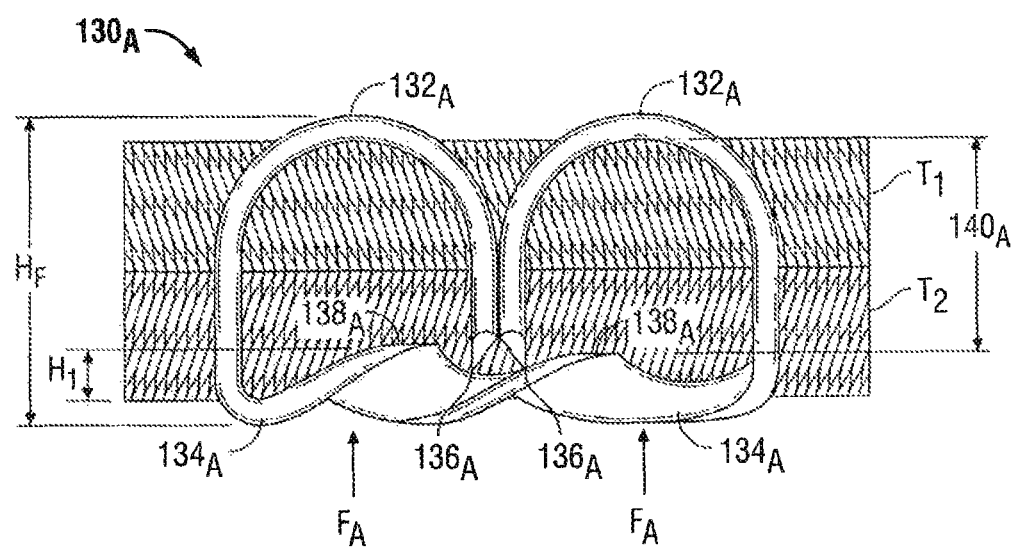
FIG. 5 is a cross-sectional view of the surgical fastener shown in FIG. 4 formed within adjacent tissue segments.
Figure 6:
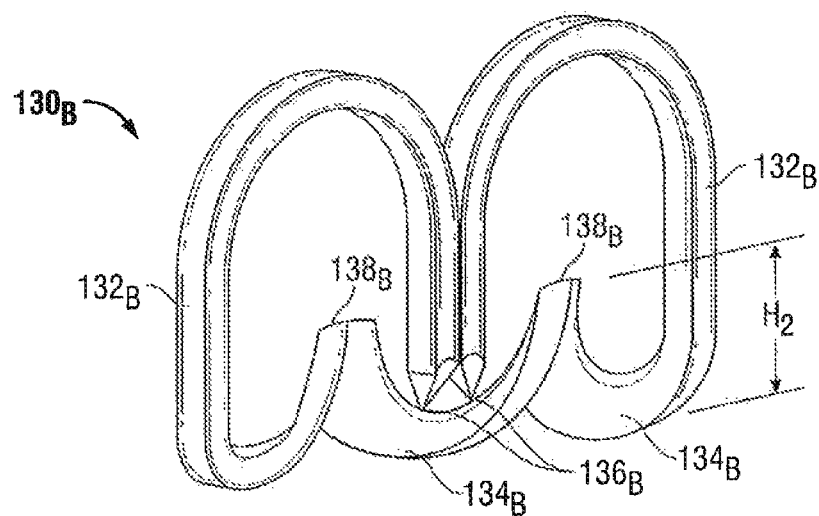
FIG. 6 is a side, perspective view of another alternative embodiment of the surgical fastener shown in FIG. 2 including a twisted backspan with a plurality of protrusions defining a second, greater height.
Figure 7:
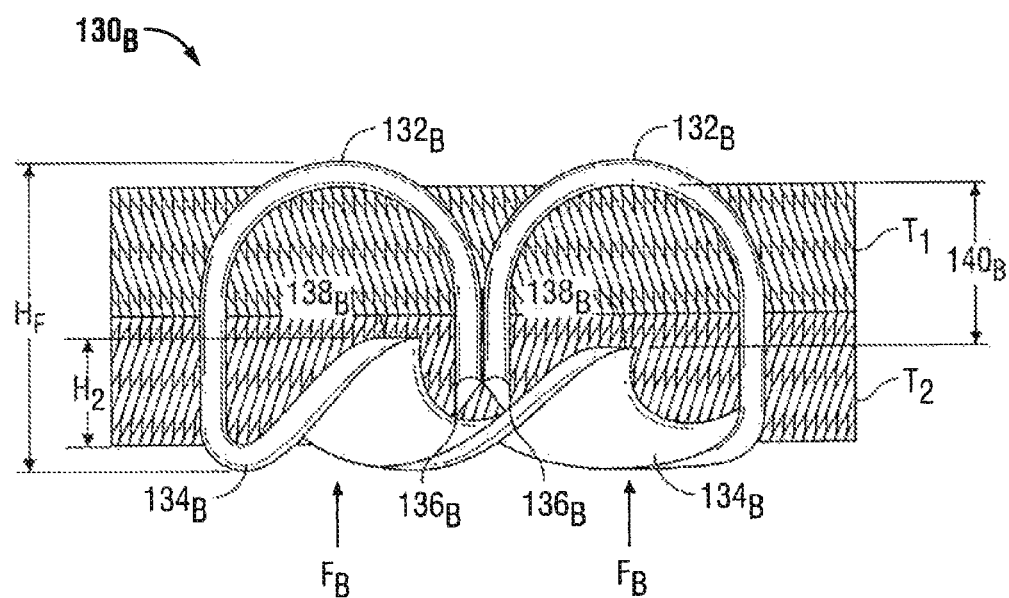
FIG. 7 is a cross-sectional view of the surgical fastener shown in FIG. 6 formed within adjacent tissue segments.

FIGS. 4-7 illustrate alternative configurations for the surgical fastener 130 shown in FIG. 2 that will be identified generally by the reference characters $130_A$ (FIGS. 4, 5) and $130_B$ (FIGS. 6, 7). The surgical fastener $130_A$ includes a non-linear twisted backspan $134_A$ defining one or more projections $138_A$, and the surgical fastener $130_B$ includes a non-linear twisted backspan $134_B$ defining one or more projections $138_B$, such that the backspans $134_A$, $134_B$ are substantially non-linear in configuration. The surgical fastener backspans $134_A$ and $134_B$ differ in configuration in that they have different heights as described in more detail below. When formed, the substantially non-linear configuration of the twisted backspans $134_A$, $134_B$ further restricts the flow of blood through the tissue surrounding the surgical fasteners $134_A$, $134_B$ upon formation when compared to the substantially linear backspan 134 of the surgical fastener 130 (FIG. 2).

Referring now to FIGS. 4, 5 in particular, as clearly shown, the backspan $134_A$ defines a longitudinal axis about which the backspan $143_A$ rotates or twists along the length thereof. The backspan $134_A$ of the surgical fastener $130_A$ includes two projections $138_A$ defined by the twisted configuration thereof. It should be appreciated that although the backspan has a twist that defines two projections $138_A$, it is also contemplated that further twists could be provided to define additional projections $138_A$. The projections $138_A$ extend from the backspan $134_A$ in the direction of the penetrating ends $136_A$ of the legs $132_A$, and define a first height "$H_1$" that is measured from the top of the projection $138_A$ to the outermost curve of the backspan $134_A$. When the surgical fastener $130_A$ is formed within the tissue segments "$T_1$," "$T_2$," the projections $138_A$ cooperate with the legs $132_A$ of the surgical fastener $130_A$ to apply a compressive force "$F_A$" thereto. The compressive force "$F_A$" applied by the surgical fastener $130_A$ is greater than the compressive force "F" applied by surgical fastener 130 (FIG. 3), as the compressive space $140_A$ defined between the backspan $134_A$ and the legs $132_A$ and occupied by the tissue segments "$T_1$," "$T_2$" is less in the surgical fastener $130_A$ when compared to the compressive space 140 (FIG. 3) occupied by the tissue segments "$T_1$," "$T_2$" upon formation of the surgical fastener 130. Accordingly, when compared to the surgical fastener 130, the surgical fastener $130_A$ applies greater pressure to the tissue segments "$T_1$," "$T_2$". Consequently, the flow of blood through the tissue surrounding the surgical fastener $130_A$ upon formation will be more restricted when compared to the flow of blood through the tissue surrounding surgical fastener 130 upon formation, thereby further facilitating hemostasis. The dimensions of the projections $138_A$ and the compressive space $140_A$ occupied by the tissue segments "$T_1$," "$T_2$" are such that blood flow is not completely restricted, however, thereby preventing against any unnecessary necrosing of tissue. When formed, the surgical fastener $130_A$ defines an overall height "$H_F$" (measured from the backspan $134_A$ to the outermost curve of the formed legs $132_A$) that is substantially equal to that defined by the surgical fastener 130 (FIG. 3).

Referring now to FIGS. 6, 7, the backspan $134_B$ of the surgical fastener $130_B$ includes two projections $138_B$ defined by the twisted configuration thereof. It should be appreciated that although the backspan $138_B$ has a twist that defines two projections $138_B$, it is also contemplated that further twists could be provided to define additional projections $138_B$. The projections $138_B$ extend from the backspan $134_B$ in the direction of the penetrating ends $136_B$ of the legs $132_B$ to define a second height "$H_2$" that is greater than the height "$H_1$" of the projections $134_A$ extending outwardly from the backspan $134_A$ of surgical fastener $130_A$ illustrated in FIGS. 4, 5. Accordingly, when the surgical fastener $130_B$ is formed within tissue segments "$T_1$," "$T_2$" (FIG. 7), the projections $138_B$ cooperate with the legs $132_B$ of the surgical fastener $130_B$ to apply a compressive force "$F_B$" thereto that is greater than the compressive forces "F" (FIG. 3), "$F_A$" (FIG. 5) respectively applied by the surgical fasteners 130, $130_A$, as the compressive space $140_B$ (FIG. 7) occupied by the tissue segments "$T_1$," "$T_2$" upon formation of the surgical fastener $130_B$ is less than the compressive spaces 140 (FIG. 3) and $140_A$ (FIG. 5) respectively occupied by the tissue segments "$T_1$," "$T_2$" upon formation of the surgical fasteners 130, $130_A$. Accordingly, when compared to the surgical fasteners 130, $130_A$, the surgical fastener $130_B$ applies greater pressure to the tissue segments "$T_1$," "$T_2$." Consequently, the flow of blood through the tissue surrounding the surgical fastener $130_B$ upon formation will be more restricted when compared to the flow of blood through the tissue surrounding surgical fasteners 130, $130_A$ upon formation. The dimensions of the projections $138_B$ and the compressive space $140_B$ occupied by the tissue segments "$T_1$," "$T_2$" are such that blood flow is substantially, if not completely restricted, thereby further facilitating, and effectuating hemostasis. When formed, the surgical fastener $130_B$ defines an overall height "$H_F$" that is substantially equal to those defined by the surgical fasteners 130 (FIG. 3), $130_A$ (FIG. 5).

The surgical fasteners $130_A$, $130_B$ shown in FIGS. 4-7 are substantially similar but for the dimensions of the one or more projections $138_A$, $138_B$, formed in their respective backspans $134_A$, $134_B$. The respective dimensions "$H_1$," "$H_2$" of the projections $138_A$, $138_B$ as well as the dimensions of the compressive spaces $140_A$, $140_B$ occupied by tissue segments "$T_1$," "$T_2$" when the respective surgical fasteners $130_A$, $130_B$ are formed, may be altered or varied in different embodiments to effectuate any desired level of hemostasis and blood flow in the tissue segments "$T_1$," "$T_2$" dependent upon the attributes of the tissue, e.g., the thickness thereof, or the presence of scar tissue.

Figure 8:
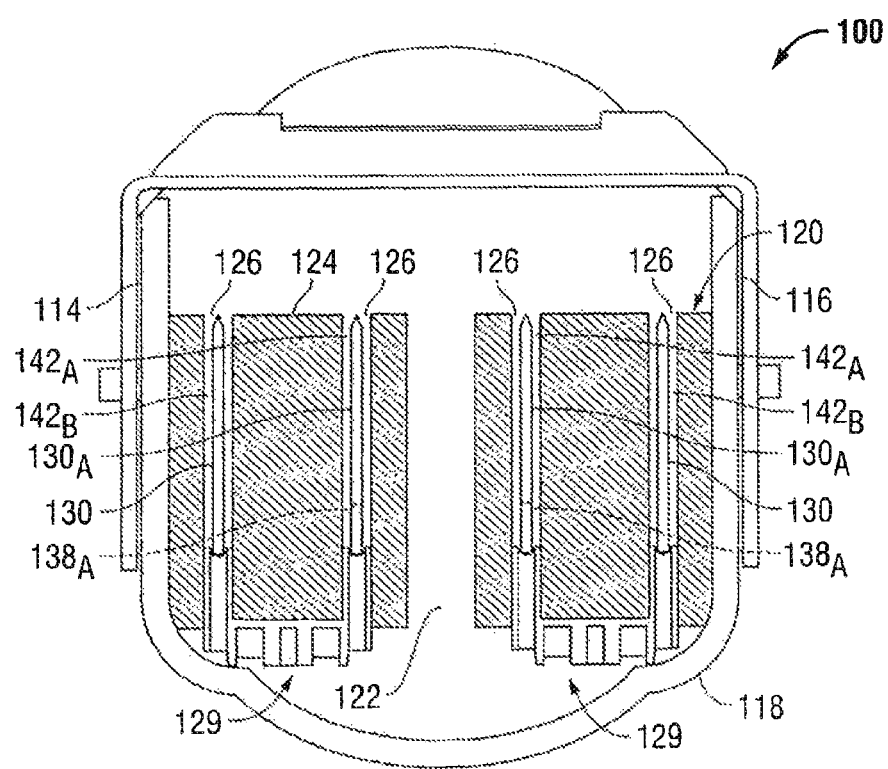
FIG. 8 is an axial, cross-sectional view taken through line 8-8 in FIG. 1, which illustrates the surgical fastener cartridge loaded with the surgical fasteners seen in FIGS. 2-5, wherein the surgical fasteners shown in FIGS. 4, 5 are arranged in a pair of inner rows and the surgical fasteners shown in FIGS. 2, 3 are arranged in a pair of outer rows.
Figure 9:
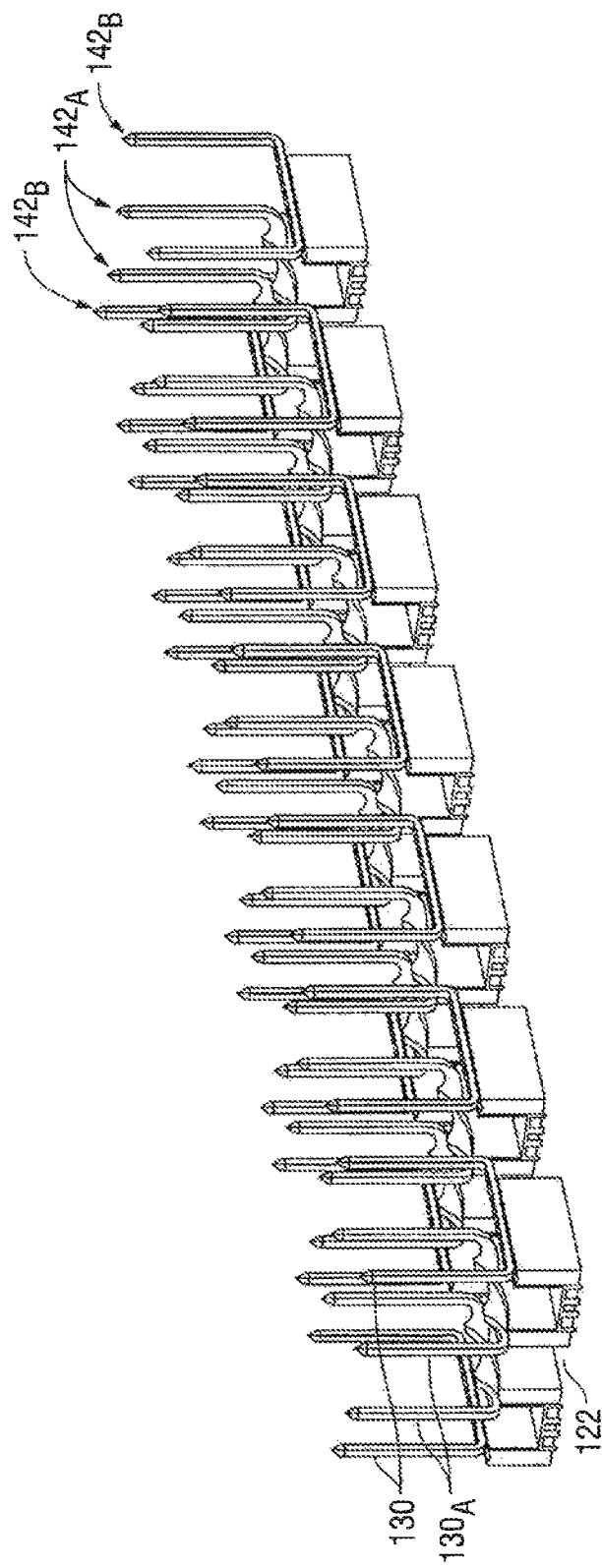
FIG. 9 is a partial, longitudinal, perspective view, with parts removed, of the surgical fastener cartridge seen in FIG. 8 illustrating the plurality of surgical fasteners arranged into inner and outer rows.
Figure 10:
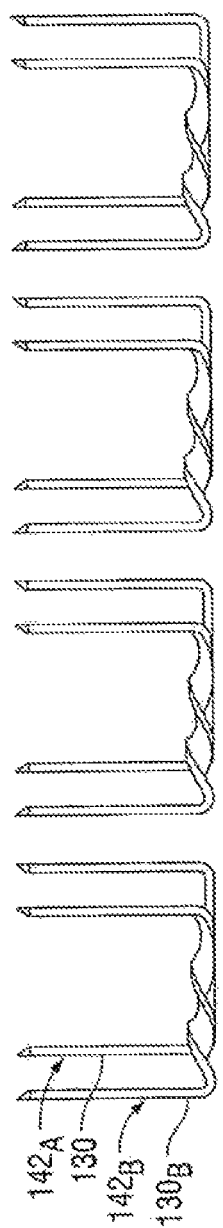
FIG. 10 is a partial, longitudinal, cross-sectional view of the surgical fastener cartridge of seen in FIG. 8 taken through line 10-10 in FIG. 1, which illustrates an inner and outer row of surgical fasteners.
Figure 11:
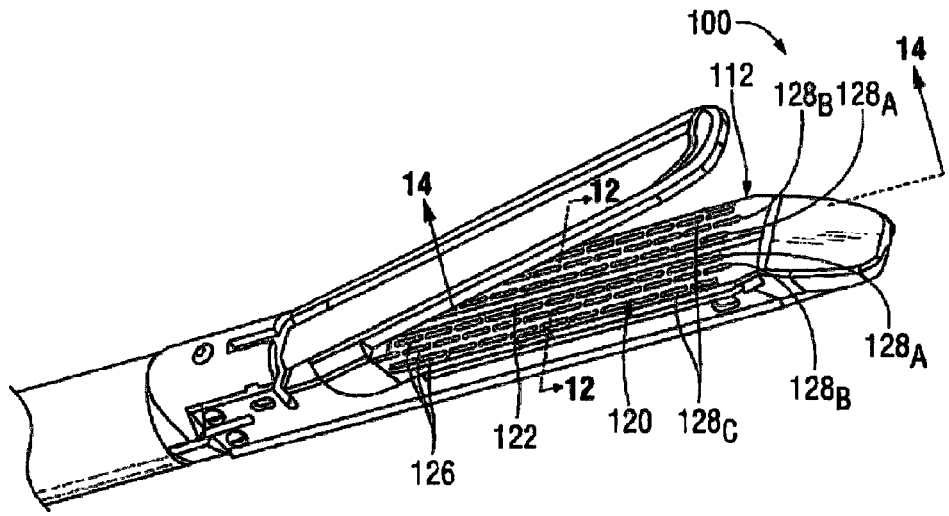
FIG. 11 is a top, perspective view of an alternative embodiment of the surgical fastener cartridge seen in FIG. 1 loaded with a plurality of surgical fasteners arranged into inner rows, intermediate rows, and outer rows.

FIGS. 8-10 illustrate the surgical fasteners 130, $130_A$ installed within the cartridge body 112 shown in FIG. 1. The surgical fasteners 130, $130_A$ are arranged within the cartridge body 112 to define a pair of first (inner) rows $142_A$ and a pair of second (outer) rows $142_B$ that correspond to the respective inner and outer rows $128_A$, $128_B$ of fastener retention slots 126 formed in the top wall 120 (FIG. 1). Accordingly, the pair of inner rows $142_A$ are spaced laterally from the knife slot 122, on opposite sides thereof, and the pair of outer rows $142_B$ are spaced laterally from the pair of inner rows $142_A$ (further away from the central longitudinal axis of the cartridge), again on opposite sides of the knife slot 122. As such, the surgical fasteners 130, $130_A$ will be deployed on opposite sides of the cut-line (not shown) created in the tissue upon fastening. That is, the surgical fasteners $130_A$, which include the aforedescribed projections $138_A$ (FIGS. 4, 5), provide a greater compressive force to the tissue, since there is a shorter distance between the projections $138_A$ and the curve of the formed legs 132, and accordingly, are provided in the inner rows $142_A$ closer to the cut-line. The fasteners 130, which define a greater distance between the curve of the legs 132 and the backspan 134 upon formation, are provided in the outer rows $142_B$, where the tissue might be thicker as a result of clamping the jaws of the surgical fastener applying apparatus 1000 (FIG. 1).

By positioning the fasteners providing greater tissue compression closer to the cut-line, i.e., the surgical fasteners $130_A$ in the embodiment of the surgical fastener cartridge 100 illustrated in FIGS. 8-10, a greater range of tissue thicknesses can be effectively sealed by a single cartridge. It should be appreciated however, that the present disclosure also envisions that the surgical fasteners can be positioned otherwise without departing from the scope of the present disclosure. Also, while the inner and outer rows $142_A$, $142_B$ are shown as including the surgical fasteners $130_A$, 130, respectively, the present disclosure contemplates the use of any of the surgical fasteners 130 (FIGS. 2, 3), $130_A$ (FIGS. 4, 5), $130_B$ (FIGS. 6, 7) disclosed herein, either exclusively, such that only a single type surgical fastener, e.g., surgical fastener 130, is present in a particular row, or in combination, such that a variety of surgical fasteners, e.g., surgical fasteners 130 and $130_A$, are present in the row.

As seen in FIGS. 11-14, in one embodiment, the disclosed surgical fastener cartridge 100 includes a top wall 120 having a plurality of fastener retention slots 126 arranged into a pair of first (inner) rows $128_A$ that are spaced laterally outward from the knife slot 122, a pair of second (intermediate) rows $128_B$ that are spaced laterally outward from the pair of inner rows $128_A$, and a pair of third (outer) rows $128_C$ that are spaced laterally outward (further from the central longitudinal axis) from the pair of intermediate rows $128_B$, each of which is spaced on opposite sides of the knife slot 122. In this embodiment, the fasteners, e.g., the surgical fasteners 130 (FIGS. 2, 3), $130_A$ (FIGS. 4, 5), $130_B$ (FIGS. 6, 7) are respectively arranged within the cartridge body 112 to define a pair of first (inner) rows $142_A$, a pair of second (intermediate) rows $142_B$, and a pair of third (outer) rows $142_C$ that correspond to the respective inner, intermediate, and outer rows $128_A$, $128_B$, $128_C$ of fastener retention slots 126 formed in the top wall 120 of surgical fastener cartridge 100. As with the embodiment of the surgical fastener cartridge 100 seen in FIGS. 1 and 8-10, each of the respective inner, intermediate, and outer rows $142_A$, $142_B$, $142_C$ may comprise any of the surgical fasteners 130, $130_A$, $130_B$ disclosed herein, either exclusively, such that only a single surgical fastener, e.g., surgical fastener 130, is present in a particular row, or in combination, such that a variety of surgical fasteners, e.g., surgical fasteners 130, $130_A$, and $130_B$, are present.

Figure 12:
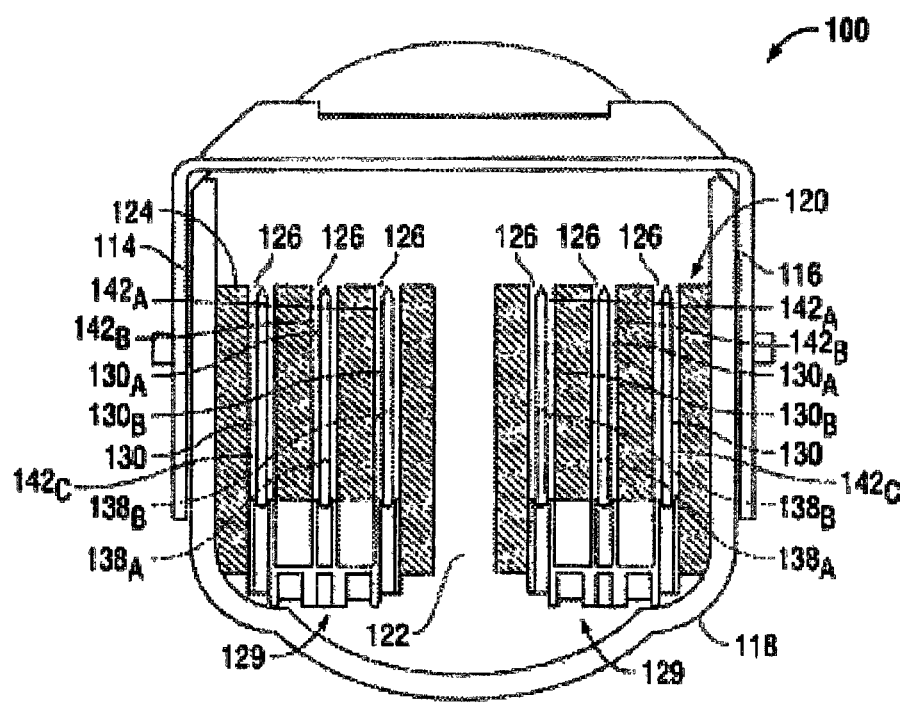
FIG. 12 is an axial, cross-sectional view taken through line 12-12 in FIG. 11, which illustrates the surgical fastener cartridge loaded with the surgical fasteners seen in FIGS. 2-7, wherein the surgical fasteners shown in FIGS. 6, 7 are arranged in the inner rows, the surgical fasteners shown in FIGS. 4, 5 are arranged in the intermediate rows, and the surgical fasteners shown in FIGS. 2, 3 are arranged in the outer rows.
Figure 13:
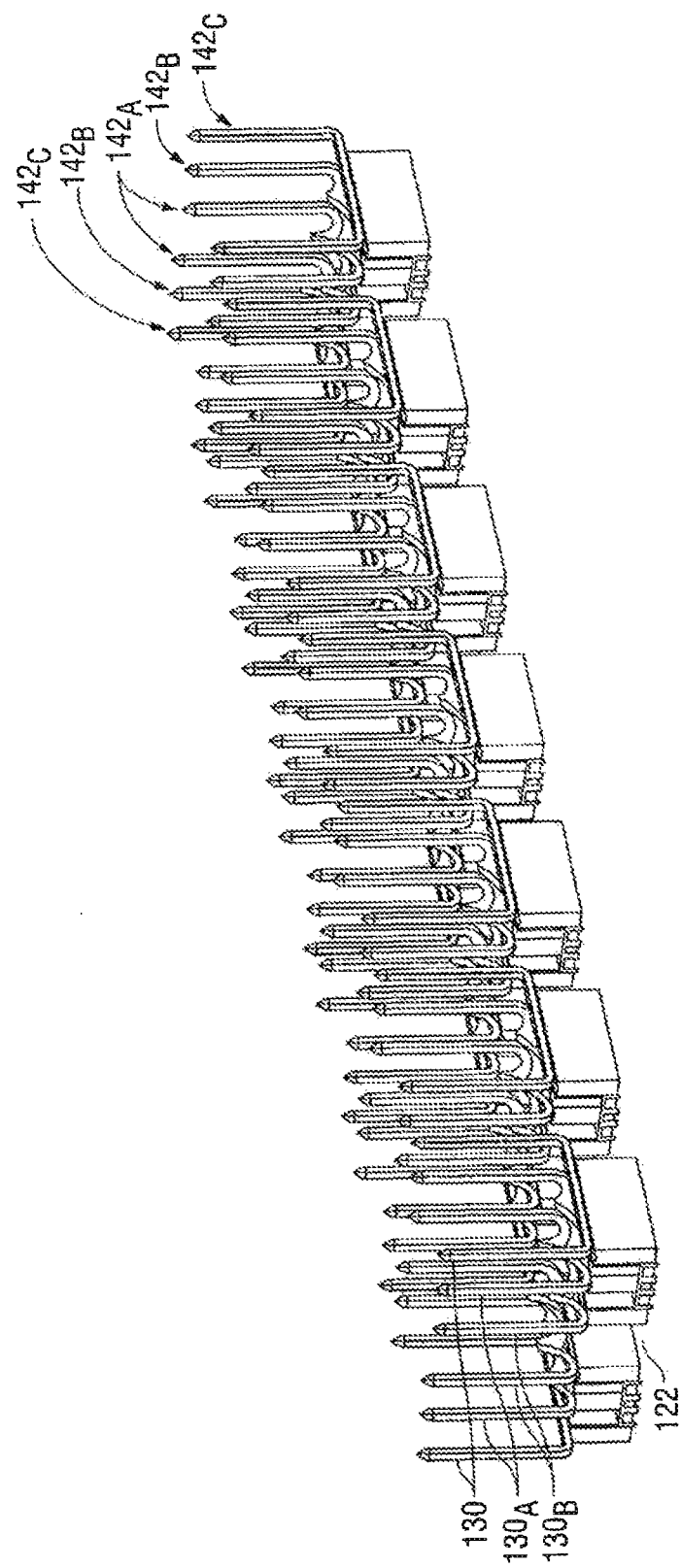
FIG. 13 is a partial, longitudinal, perspective view, with parts removed, of the surgical fastener cartridge seen in FIG. 12 illustrating the plurality of surgical fasteners arranged into inner, intermediate, and outer rows.
Figure 14:
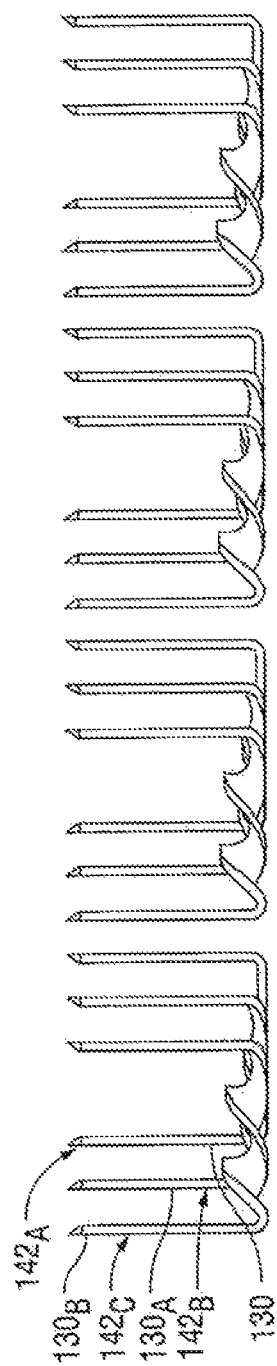
FIG. 14 is a partial longitudinal, cross-sectional view of the surgical fastener cartridge of FIG. 12 taken through line 14-14 in FIG. 11, which illustrates an inner, intermediate, and outer row of surgical fasteners.

As illustrated in FIGS. 12-14, in one particular embodiment, the outer rows $142_C$, the intermediate rows $142_B$, and the inner rows $142_A$ are comprised solely of the surgical fasteners 130, $130_A$, $130_B$, respectively, such that the flow of blood through the tissue immediately surrounding the cut-line is more restricted by the inner row $142_A$ of surgical fasteners $130_B$, whereas the flow of blood through the tissue surrounding the respective intermediate and outer rows $142_B$, $142_C$ is less restricted by surgical fasteners $130_A$, 130. Accordingly, the flow of blood will be minimized through the tissue immediately adjacent the cut-line, and will be increased gradually with the lateral distance from the cut-line. Also, by this arrangement, the surgical fasteners with the largest projections, e.g., the surgical fasteners $130_B$, will be positioned closest to the cut-line where the tissue is generally compressed to a greater extent, and the surgical fasteners providing for less compression, e.g., the surgical fasteners 130, which include a substantially linear backspan 134, will be positioned further from the cut-line where the tissue is generally compressed to a lesser extent. It is also contemplated that instead of a row of fasteners 130 with a linear backspan, a row of fasteners with a twisted backspan with a smaller height than the other twisted backspan fasteners can be utilized on the outer rows.

Figure 15:
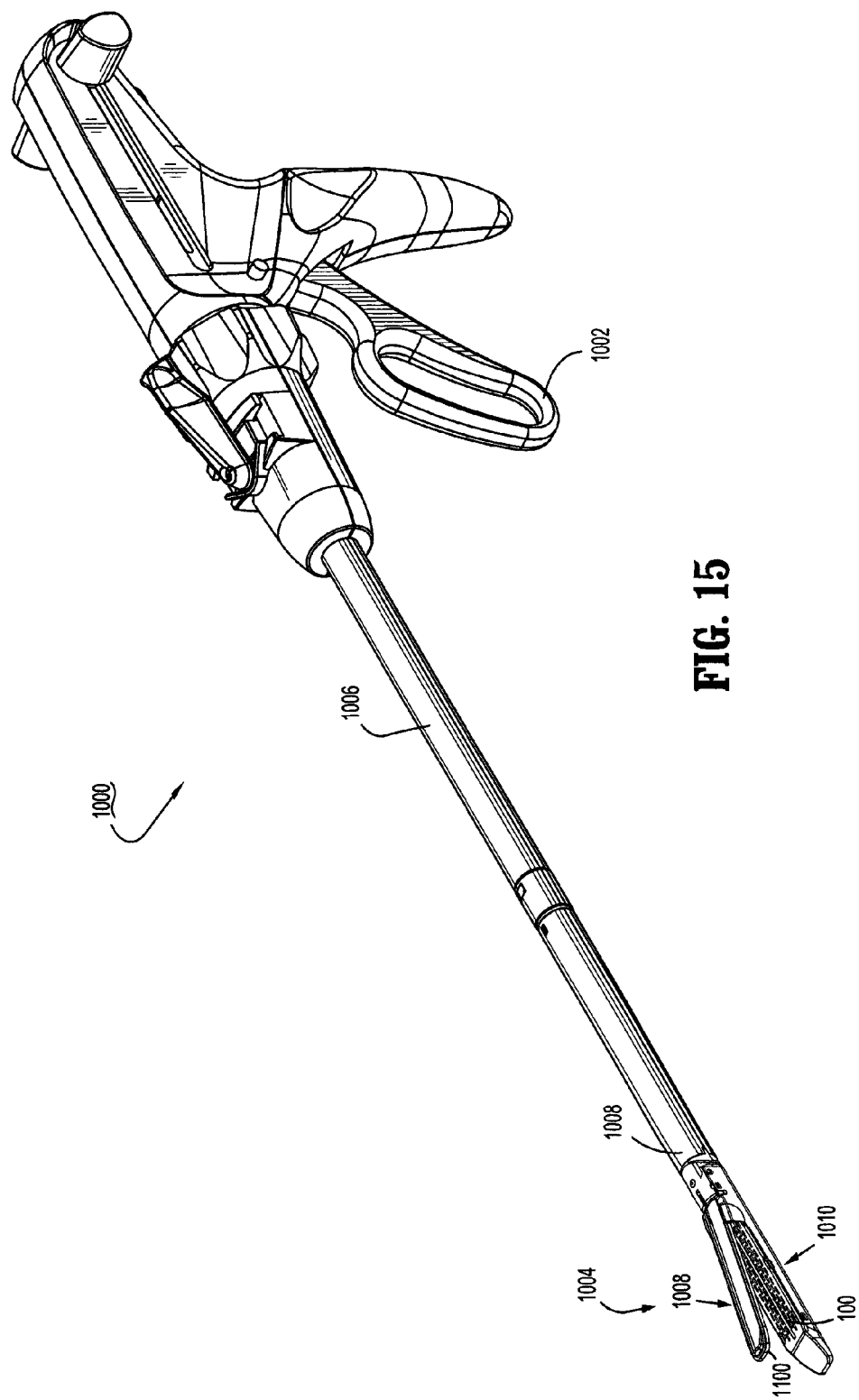
FIG. 15 illustrates an exemplary surgical fastener applying apparatus for use with the surgical fastener cartridge seen in FIG. 1 during a laparoscopic surgical procedure.
Figure 16:
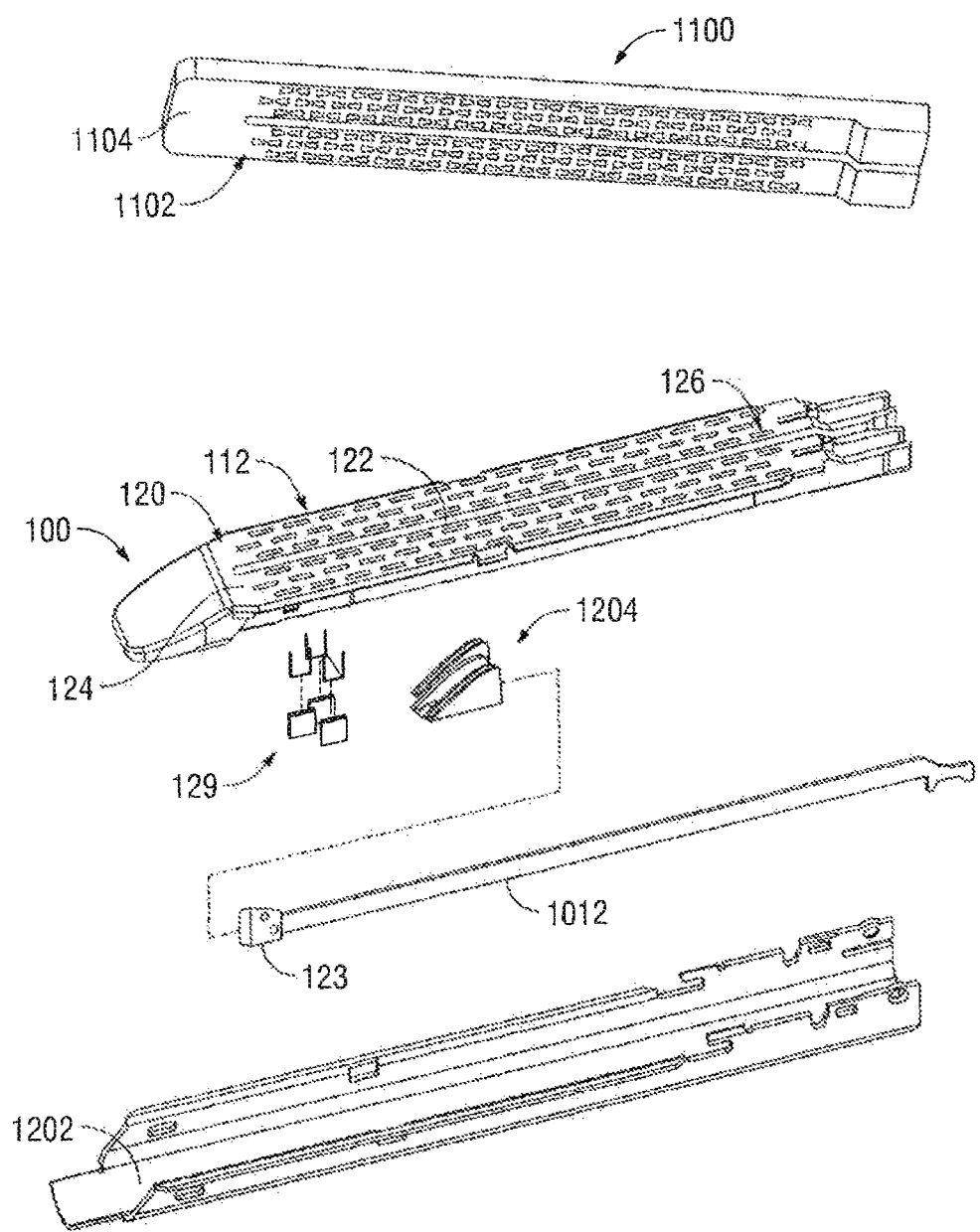
FIG. 16 is a partial, perspective view of a tool assembly of the surgical fastener applying apparatus seen in FIG. 15, with parts separated, illustrating an anvil and the surgical fastener cartridge of FIG. 1.

With reference now to FIGS. 1, 15, and 16, the surgical fastener applying apparatus 1000 will be discussed. The surgical fastener applying apparatus 1000 may be of either the re-usable or disposable variety, and includes a handle assembly 1002, with a movable handle $1003_A$ and a stationary handle $1003_B$, that is operatively connected to a tool assembly 1004 through a distally extending elongated shaft or endoscopic portion 1006. In various embodiments, the handle assembly 1002 may be manually operated, and either additionally or alternatively, may include motorized, hydraulic, ratcheting, or other such mechanisms. In general, the tool assembly 1004 is adapted to clamp, fasten together, and sever adjacent tissue segments along a cut-line.

The tool assembly 1004 includes a second jaw 1008 that is pivotally coupled to a first jaw 1010 to facilitate approximation thereof. The second jaw 1008 of the tool assembly 1004 includes an anvil 1100, and the first jaw 1010 includes a surgical fastener cartridge assembly 1200 incorporating the aforedescribed surgical fastener cartridge 100 (FIG. 1), which is loaded with a plurality of surgical fasteners, e.g., the surgical fasteners 130 (FIGS. 2, 3), the surgical fastener $130_A$ (FIGS. 4, 5), and/or the surgical fastener $130_B$ (FIGS. 6, 7), (FIGS. 2, 3). Pivoting the movable handle $1003_A$ towards the stationary handle $1003_B$ (FIG. 1) approximates the second jaw 1008 and the first jaw 1010. After the jaws 1008, 1010 are in close operative alignment clamping tissue therebetween, continued pivoting of the movable handle $1003_A$ ejects the plurality of surgical fasteners 100 (FIG. 3) from the surgical fastener cartridge 100 such that the surgical fasteners 130, $130_A$, $130_B$ are driven into the anvil 1100, thus being formed into formed surgical fasteners. The tool assembly 1004 and/or the surgical fastener cartridge assembly 1200 may comprise a removable and replaceable loading unit for the surgical fastener applying apparatus 1000.

As mentioned earlier, the surgical fastener applying apparatus 1000 includes the knife member 123. As seen in FIG. 16, the knife member 123 is operatively connected to a drive beam 1012, as described in commonly assigned U.S. Pat. No. 7,398,908, currently assigned to Tyco Healthcare Group LP, the contents of which are hereby incorporated by reference herein in its entirety. The knife member 123 may be configured and dimensioned for simultaneous engagement with both the anvil member 1100 and a cavity 1202 that is defined by the first jaw 1010.

During use, the tool assembly 1004 (FIG. 15) is first actuated to clamp onto tissue by manipulating the movable handle $1003_A$ to advance a control rod (not shown) distally. Distal advancement of the control rod results in corresponding movement of the knife member 123 (FIG. 16), and effectuates approximation of the anvil member 1100 and the surgical fastener cartridge assembly 1200. With tissue clamped between the anvil member 1100 and the surgical fastener cartridge assembly 1200, the fasteners, e.g., the surgical fastener 130 (FIGS. 2, 3), the surgical fastener $130_A$ (FIGS. 4, 5), and/or the surgical fastener $130_B$ (FIGS. 6, 7), are fired from the surgical fastener applying apparatus 1000 (FIG. 1) into the tissue. The movable handle $1003_A$ is then operated again to further advance the knife member 123 (FIG. 16).

Referring now to FIGS. 1-16, a method of fastening tissue with the surgical fastener applying apparatus 1000 (FIG. 1) will be discussed. During use, the surgical fastener applying apparatus 1000 is approximated and fired similarly to, and in accordance with other known surgical fastener applying apparatus, such as that disclosed in commonly assigned U.S. Pat. No. 5,865,361, currently assigned to Tyco Healthcare Group LP, the contents of which are hereby incorporated by reference herein in its entirety.

The movable handle $1003_A$ (FIG. 15) is operatively connected to an actuation shaft, which receives the proximal end of a control rod, such that manipulation of the movable handle $1003_A$ results in linear advancement of the actuation shaft, which causes corresponding linear advancement of the control rod. An axial drive assembly is also provided that is engagable with the control rod. More specifically, the axial drive assembly includes the elongated drive beam 1012 (FIG. 16), which includes a distal end that supports the knife member 123, and a drive member that is configured and dimensioned for engagement with the control rod. As seen in FIG. 16, the knife member 123 is positioned to translate behind a sled 1204.

After the surgical fastener applying apparatus 1000 (FIG. 15) is manipulated to position the target tissue between the open jaws 1008, 1010 of the tool assembly 1004, the jaws 1008, 1010 are approximated using the handle assembly 1002 to clamp the target tissue therebetween and apply a compressive force thereto. Specifically, manipulation of the movable handle $1003_A$ advances the actuation shaft to effectuate corresponding advancement of the control rod. Since the control rod is connected at its distal end to the drive assembly, which includes the aforementioned drive beam 1012 (FIG. 16), distal movement of the control rod causes corresponding movement of the drive beam 1012, which in turn, forces the anvil 1100 towards the surgical fastener cartridge assembly 1200.

With the tissue securely clamped between the jaws 1008, 1010 (FIG. 15), the surgical fastener applying apparatus 1000 is then fired to eject the surgical fasteners, e.g., the surgical fasteners, e.g., the surgical fastener 130 (FIGS. 2, 3), the surgical fastener $130_A$ (FIGS. 4, 5), and/or the surgical fastener $130_B$ (FIGS. 6, 7). To fire the surgical fastener applying apparatus 1000 (FIG. 15), the movable handle $1003_A$ is again manipulated to cause advancement of the drive assembly, which causes the sled 1204 (FIG. 16) to traverse the cartridge body 1202, and eject the plurality of surgical fasteners 130, $130_A$, $130_B$ from the surgical fastener cartridge 100 (FIG. 1). More specifically, as the sled 1204 moves distally, it engages the pushers 129 (FIGS. 8, 12, 16) to thereby drive the surgical fasteners 130, $130_A$, $130_B$ upwardly, i.e., towards the top wall 120 (FIG. 1) of the surgical fastener cartridge 100. As the surgical fasteners 130, $130_A$, $130_B$ are driven upwardly, the fastener retention slots 126 maintain the relative positions thereof.

After passing through the fastener retention slots 126, the surgical fasteners 130, $130_A$, $130_B$ pass through the tissue and are forced into engagement with pockets 1102 formed in a tissue contacting surface 1104 of the anvil 1100, thereby achieving, for example, the formed configurations seen in FIGS. 3, 5, and 7, respectively. Upon formation within the tissue, the surgical fasteners 130, $130_A$, $130_B$ limit the blood flow through the tissue immediately adjacent and surrounding the cut-line to thereby effectuate hemostasis, while permitting greater blood flow through the tissue spaced laterally therefrom to minimizing necrosing of the tissue, as discussed above.

While the tool cartridge has been discussed in connection with the surgical fastener applying apparatus 1000, which is adapted for use in laparoscopic procedures for performing surgical anastomotic fastening of tissue, the cartridge may be adapted for use with any surgical instrument suitable for the intended purpose of applying the plurality of surgical fasteners, e.g., the surgical fasteners 130, 130$_A$, 130$_B$, to a section of tissue, and thereafter, severing the tissue along a cut-line.

Figure 17:
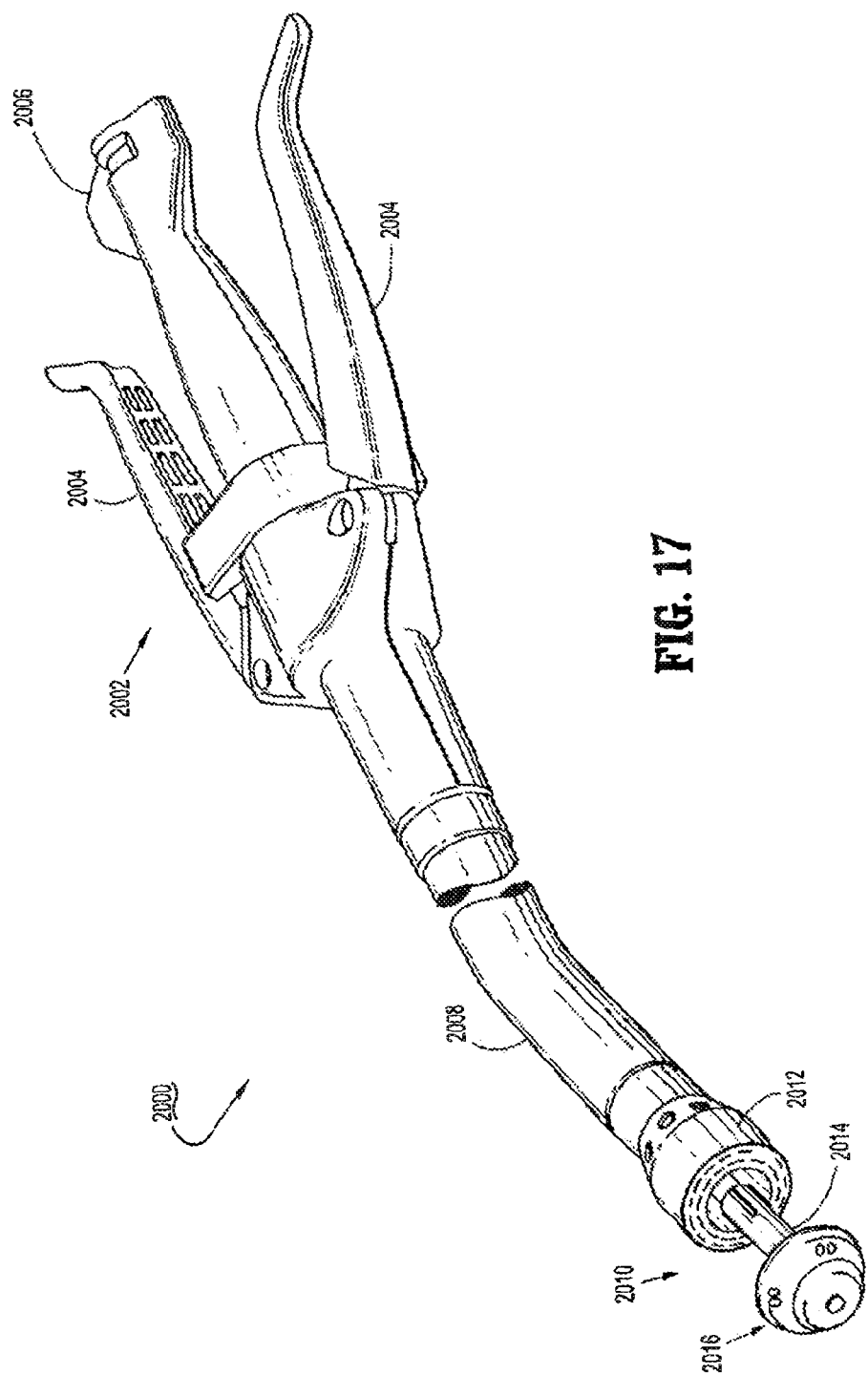
FIG. 17 illustrates an end-to-end anastomosis device for use with an alternative embodiment of the surgical fastener cartridge seen in FIG. 1 during a surgical anastomosis procedure.

For example, the tool assembly 1004 (FIG. 15) may be adapted for use with an end-to-end anastomosis apparatus 2000 (FIG. 17), such as that disclosed in commonly assigned U.S. Pat. No. 7,455,676, currently assigned to Tyco Healthcare Group LP, the contents of which are hereby incorporated by reference herein in its entirety. The apparatus 2000 is used to simultaneously deploy a plurality of surgical fasteners arranged in substantially annular rows. A knife is advanced with the firing of the fasteners. The apparatus 200 includes a handle assembly 2002 having a pair of actuating handle members 2004 and an approximation knob (wing nut) for moving (retracting) anvil 2016 toward cartridge 2012 containing the surgical fasteners. Cartridge 2012 is at the distal end of tubular body portion 2008 which extends from handle assembly 2002. An anvil shaft 2014 operatively couples anvil 2016 to the handle assembly 2002 such that the anvil 2016 is repositionable from a location where it is in close cooperative alignment with the fastener cartridge 2012 to a location where it is spaced apart from the fastener staple cartridge 2012.

The tool assembly 2010 includes a fastener ejection member that is positioned within the fastener cartridge 2012. The fastener ejection member includes a distal portion defining concentric rings of peripherally spaced staple pushers that are received within a respective staple retention slot to eject the surgical fasteners from the fastener cartridge 2012. The fastener ejection member is configured and dimensioned to be contacted by a distal end of a driver tube that is operatively connected to handle members 2004 through the body portion 2008 such that manipulation effectuates advancement of the driver tube to force the staple pushers into engagement with the plurality of surgical fasteners retained with in the fastener cartridge 2012 to cause ejection of the fasteners through tissue and into contact with the anvil pockets of the anvil 2016, providing varying compressive forces on the tissue due to the varying configurations of the fastener.

Figure 18:
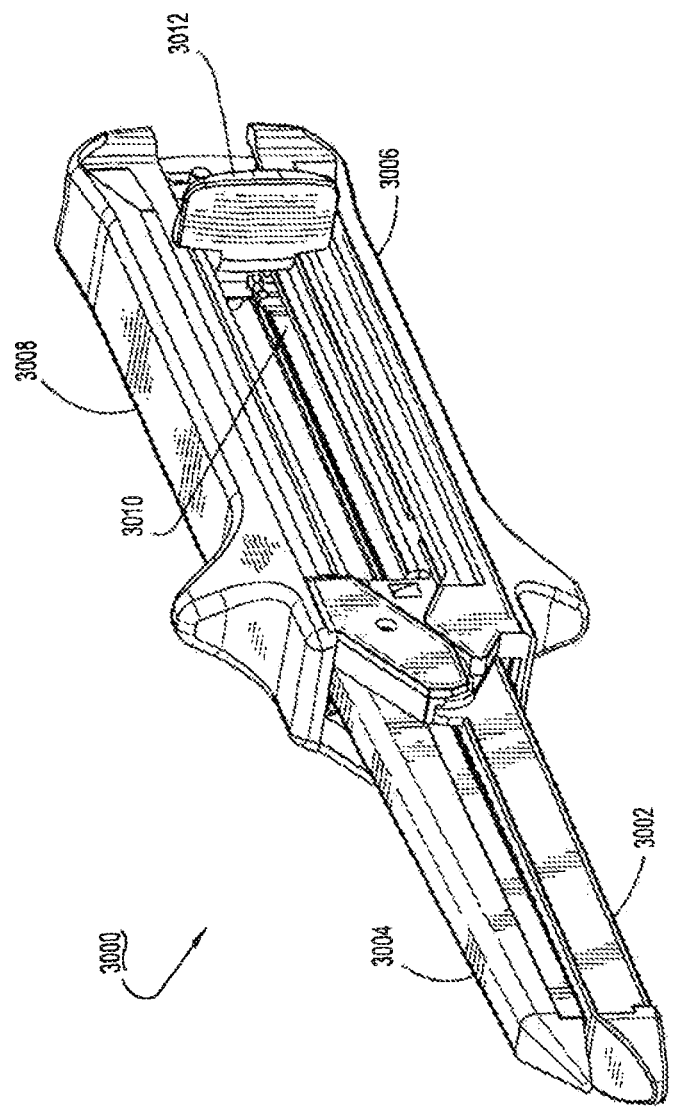
FIG. 18 illustrates a surgical fastener applying instrument for use with yet another alternative embodiment of the surgical fastener cartridge seen in FIG. 1 during an open gastrointestinal anastomotic fastening procedure.

The tool assembly 1004 (FIG. 15) may also be adapted for use with a surgical stapling apparatus 3000 (FIG. 18), such as that disclosed in commonly assigned U.S. Pat. No. 7,334,717, the contents of which are hereby incorporated by reference herein in its entirety. The surgical stapling apparatus 3000 includes a cartridge receiving half-section 3002, which accommodates a plurality of surgical fasteners arranged in a plurality of substantially linear rows, and an anvil half-section 3004 containing a plurality of anvil pockets arranged in corresponding rows. The half-sections 3002, 3004 are pivotally connected via handles 3006, 3008 for approximation during use.

Following approximation of the half-sections 3002, 3004 to clamp tissue therebetween, the surgical fastener applying apparatus 3000 is fired by advancing firing mechanism 3010 distally by the advancement of a firing knob 3012. Distal movement of the firing mechanism 3010 causes a plurality of cam bars to engage camming surfaces that interact with a plurality of pushers to expel the plurality of surgical fasteners from the cartridge receiving half-section 3002 through tissue into contact with the anvil pockets of the anvil portion 3004, providing varying compressive forces on the tissue due to the varying configurations of the fasteners. The surgical fasteners are positioned on either side of a track which guides a knife during longitudinal movement to thereby sever tissue along a cut-line.

Figure 19:
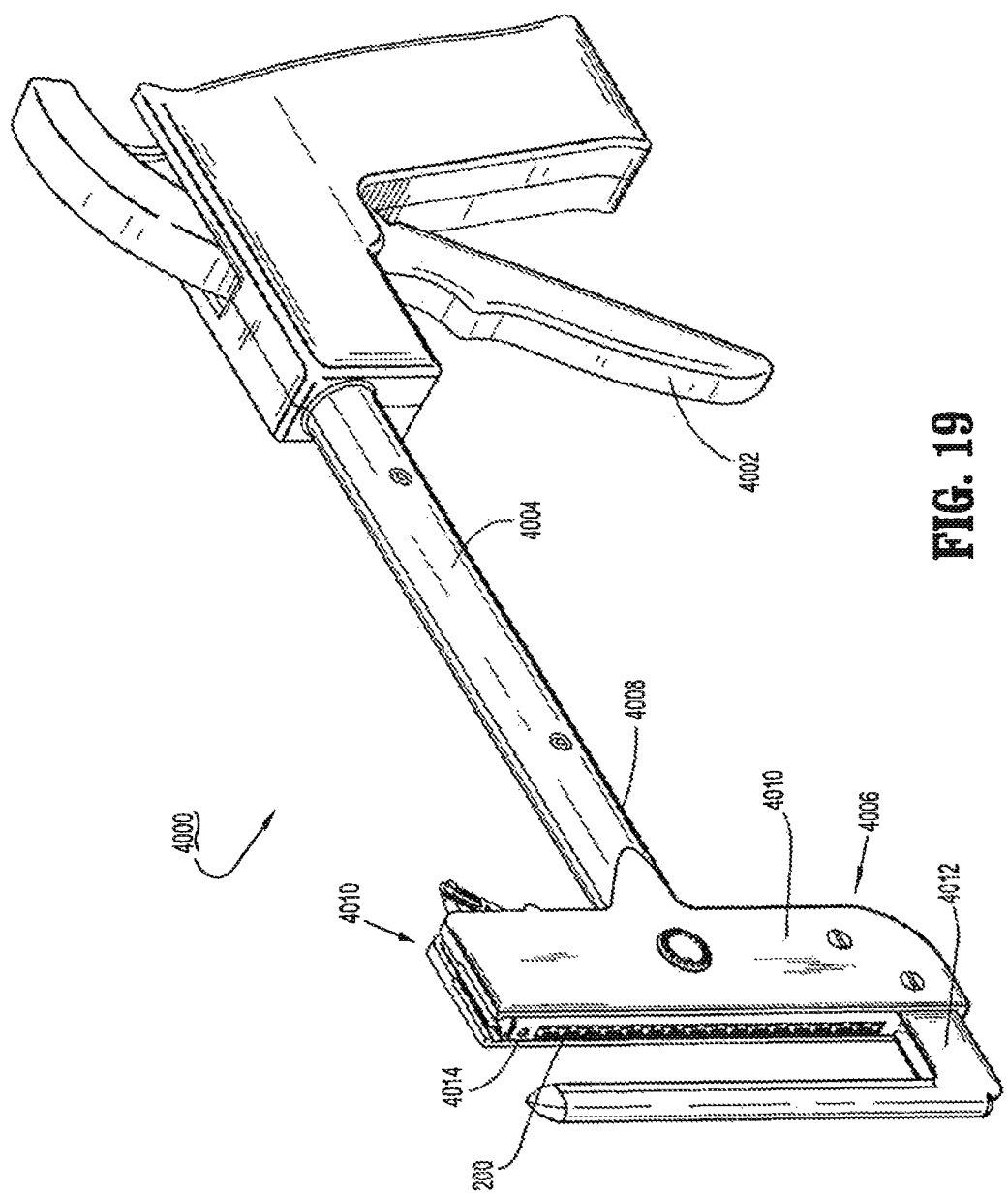
FIG. 19 illustrates a transverse anastomosis fastener applying instrument for use with an alternative embodiment of the surgical fastener cartridge shown in FIG. 18.

The tool assembly 1004 (FIG. 15) may also be adapted for use with a transverse anastomosis fastening instrument 4000 (FIG. 19), such as that disclosed in commonly owned U.S. Pat. Nos. 5,964,394 and 7,070,083, the contents of which are hereby incorporated by reference herein in their entirety. The surgical fastener applying apparatus 4000 includes an approximation lever 4001, a movable handle 4002, and an elongated portion 4004 that extends distally from the handle 4002. The cartridge 200, containing a plurality of fasteners arranged in substantially linear rows transverse to a longitudinal axis of the instrument, is supported within cartridge receiving portion 4014 of frame 4006.

Prior to firing of the surgical fastener applying apparatus 4000, the approximation lever 4001 is actuated to distally advance a drive member that is operatively connected to the surgical fastener cartridge 200 to move the surgical fastener cartridge 200 towards the anvil 4012, which remains stationary, and capture tissue therebetween. Thereafter, the handle 4002 is moved to advance a pusher bar distally through the elongated portion 4004 to cause corresponding movement of a head portion included at the distal end of the pusher bar. The head portion includes a plurality of fingers extending distally therefrom that are configured and dimensioned to engage the cartridge assembly to thereby eject the plurality of surgical fasteners retained therein through tissue and into contact with the anvil pockets of anvil 4012 for formation, providing varying compressive forces on the tissue due to the varying diameters. A knife can be provided in the apparatus.

It is also envisioned that the tool assembly 1004 (FIG. 1) may also be adapted for use with any of the other surgical fastener applying apparatus discussed in commonly owned U.S. Pat. Nos. 6,045,560; 5,964,394; 5,894,979; 5,878,937; 5,915,616; 5,836,503; 5,865,361; 5,862,972; 5,817,109; 5,797,538; and 5,782,396, the disclosures of which are hereby incorporated by reference herein in their entirety.

In additional embodiments of the present disclosure, the surgical fastener applying apparatus may include a plurality of cam bars for interacting with the pushers to deploy the surgical fasteners. For example, the surgical fastener applying apparatus disclosed in U.S. Pat. No. 5,318,221, the disclosure of which is hereby incorporated by reference herein, in its entirety, has a cam bar adapter that holds a plurality of cam bars and a knife. A channel is advanced through operation of the handle of the apparatus, which drives the cam bars and knife forward. A clamp tube that surrounds the proximal end of the anvil is advanced to clamp the anvil and cartridge together. In another example, the surgical fastener applying apparatus disclosed in U.S. Pat. No. 5,782,396, the disclosure of which is hereby incorporated by reference herein, in its entirety, has an actuation sled. An elongated drive beam is advanced distally through operation of the handle of the apparatus, driving the actuation sled forward. The distal end of the drive beam engages the anvil and the channel that supports the cartridge as the drive beam travels distally, to deploy the staples and clamp the anvil and cartridge together.

Figure 20:
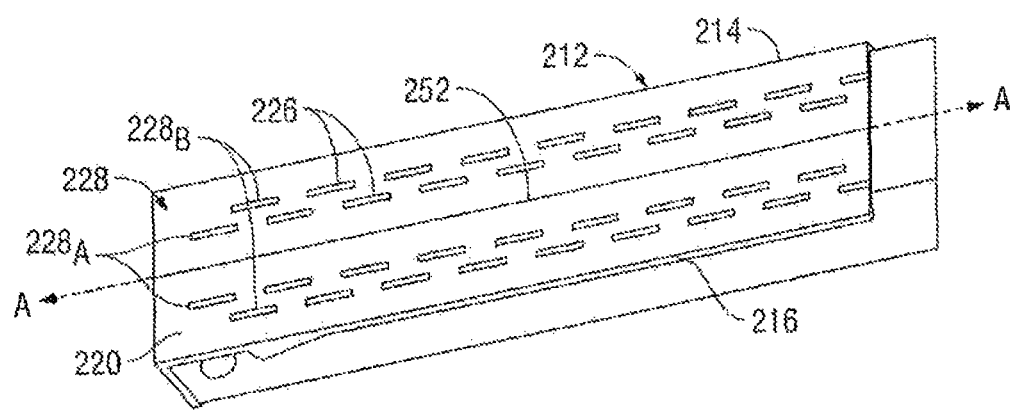
FIG. 20 is a top, perspective view of another alternative embodiment of the surgical fastener cartridge seen in FIG. 1 according to the principles of the present disclosure.

Referring now to FIG. 20, an alternative embodiment of the surgical fastener cartridge, identified generally by the reference character 200, will be discussed. The surgical fastener cartridge 200 is substantially similar to the surgical fastener cartridge 100 discussed above, and accordingly, will only be discussed with respect to its differences therefrom.

The surgical fastener cartridge 200 is loaded with a plurality of surgical fasteners that are arranged into one or more rows, as in the case of the aforedescribed surgical fastener cartridge 100. However, in contrast to the surgical fastener cartridge 100, the surgical fastener cartridge 200 does not include a knife slot for the accommodation of a knife or other such cutting element, although an alternative embodiment including a knife slot would be within the scope of the present disclosure. The surgical fastener cartridge 200 includes a plurality of fastener retention slots 226 on a top wall 220 of a cartridge body 212 that are arranged into a plurality of rows 228. The rows 228 of retention slots 226 are spaced laterally from a centerline 252 extending along the longitudinal axis "A-A" defined by cartridge body 212, and may be positioned equidistant from the sidewalls 214, 216. As shown, the plurality of rows 228 includes a pair of first (inner) rows $228_A$ that are disposed on opposite sides of the centerline 252, and a pair of second (outer) rows $228_B$ that are spaced laterally outward from the pair of inner rows $228_A$, (further from the central longitudinal axis of the cartridge), again on opposite sides of the centerline 252. Each of the fastener retention slots 226 is configured and dimensioned to receive one of a plurality of surgical fasteners, e.g., the surgical fasteners 130 (FIGS. 2, 3), $130_A$ (FIG. 4, 5), or $130_B$ (FIGS. 6, 7) and pushers 129 (FIG. 8) therein such that the surgical fasteners are deployed in rows, e.g., inner and outer rows in the embodiment of the surgical fastener cartridge 200 shown of FIG. 20, on opposite sides of the centerline 252.

Although the surgical fastener cartridge 200 is depicted as including pairs of first and second rows $228_A$, $228_B$, respectively, additional rows of fastener retention slots 226, and accordingly, additional rows of surgical fasteners, may be included in alternative embodiments of the surgical fastener cartridge 200, as discussed above with respect to surgical fastener cartridge 100. Also, it is envisioned that the fasteners may be arranged within the surgical fastener cartridge 200 in any of the various exemplary configurations discussed above with respect to the surgical fastener cartridge 100, for example.

Reference will now be made to FIGS. 21-24, which illustrate alternative configurations for the surgical fastener 130 shown in FIG. 2 that will be identified generally by the reference characters $130_C$ (FIGS. 21, 22) and $130_D$ (FIGS. 23, 24), that may be loaded into the surgical fastener cartridge 100 shown in FIGS. 1, 8, for example and used with the various apparatus described herein. The surgical fastener $130_C$ includes a non-linear backspan $134_C$ with one or more recesses $138_C$ formed therein. The recesses $138_C$ form curved portions extending inwardly from the backspan $134_C$, i.e., towards the penetrating ends $136_C$ in the unformed condition, in arcuate fashion to define one or more humps having a first height "$H_1$" that act to restrict the flow of blood through the tissue surrounding the surgical fastener $130_C$. As shown, in the formed condition of the fastener, the backspan preferably has a first curved portion opposite the curve of one of the legs and a second curved portion opposite the curve of the other fastener leg.

Figure 22:
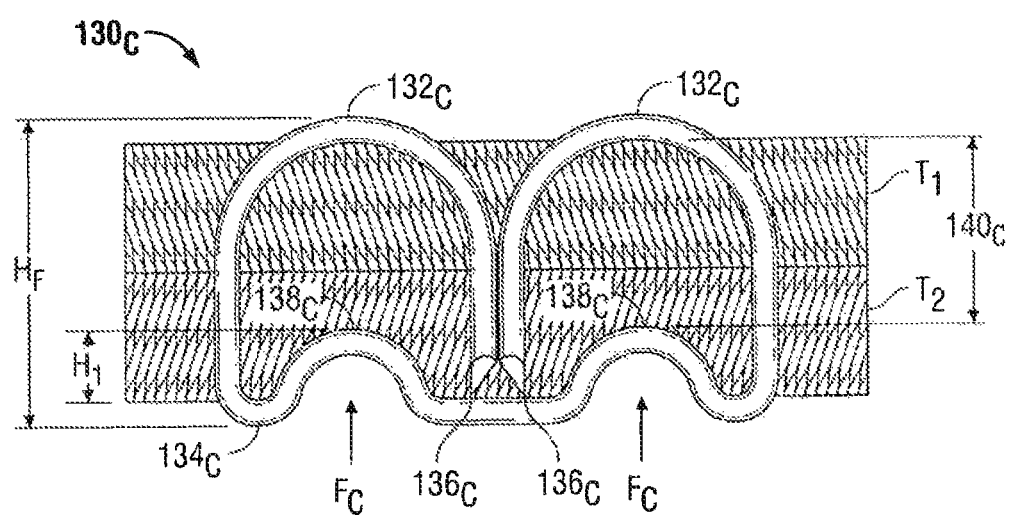
FIG. 22 is a cross-sectional view of the surgical fastener shown FIG. 21 formed within adjacent tissue segments.

When the surgical fastener $130_C$ is formed within tissue segments "$T_1$," "$T_2$," as seen in FIG. 22 for example, the curves (humps) $138_C$ cooperate with the legs 132 of the surgical fastener $130_C$ to apply a compressive force "$F_C$" thereto. The compressive force "$F_C$" applied by the surgical fastener $130_C$ is greater than the compressive force "F" applied by surgical fastener 130 (FIG. 3), as the compressive space $140_C$, which is defined between the backspan $134_C$ and the legs $132_C$ and occupied by the tissue segments "$T_1$," "$T_2$," is less in the surgical fastener $130_C$ when compared to the compressive space 140 (FIG. 3) occupied by the tissue segments "$T_1$," "$T_2$" in the surgical fastener 130. Accordingly, greater pressure is applied to the tissue segments "$T_1$," "$T_2$" by surgical fastener $130_C$. Consequently, the flow of blood through the tissue surrounding the surgical fastener $130_C$ is more restricted when compared to the flow of blood through the tissue surrounding surgical fastener 130 (FIG. 3), thereby further facilitating hemostasis. The dimensions of the recesses/curves $138_C$ and the compressive space $140_C$ occupied by the tissue segments "$T_1$," "$T_2$" are such that blood flow is not completely restricted, however, thereby preventing any unnecessary necrosing of tissue. When formed, the surgical fastener $130_C$ defines an overall height "$H_F$" (measured from the backspan $134_C$ to the outermost curved of the formed legs $132_C$) that is substantially equal to that defined by the surgical fastener 130 (FIG. 3).

Figure 21:
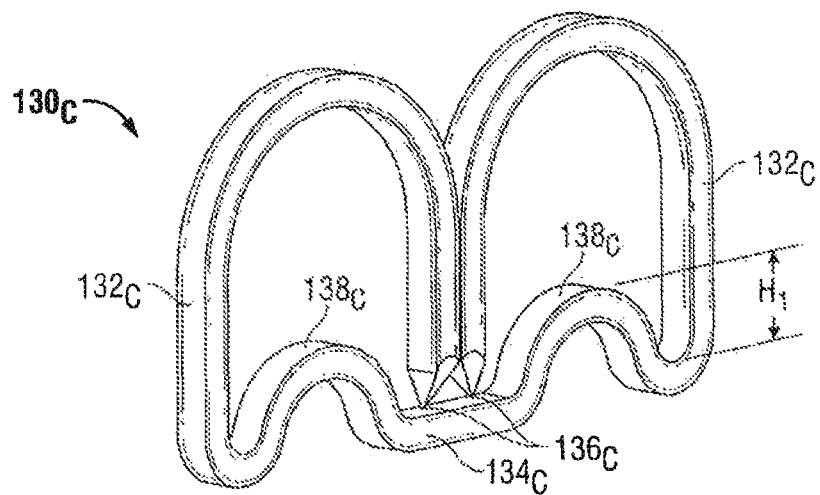
FIG. 21 is a side, perspective view of an alternative embodiment of the surgical fastener shown in FIG. 2 including a backspan with a plurality of recesses forming projections and defining a first height.
Figure 23:
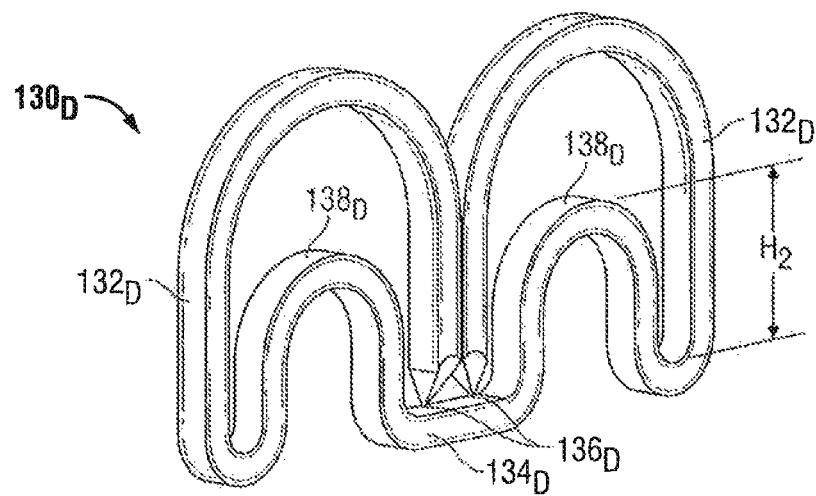
FIG. 23 is a side, perspective view of another alternative embodiment of the surgical fastener shown in FIG. 2 includ-ing a backspan with a plurality of recesses forming projections defining a second, greater height.
Figure 24:
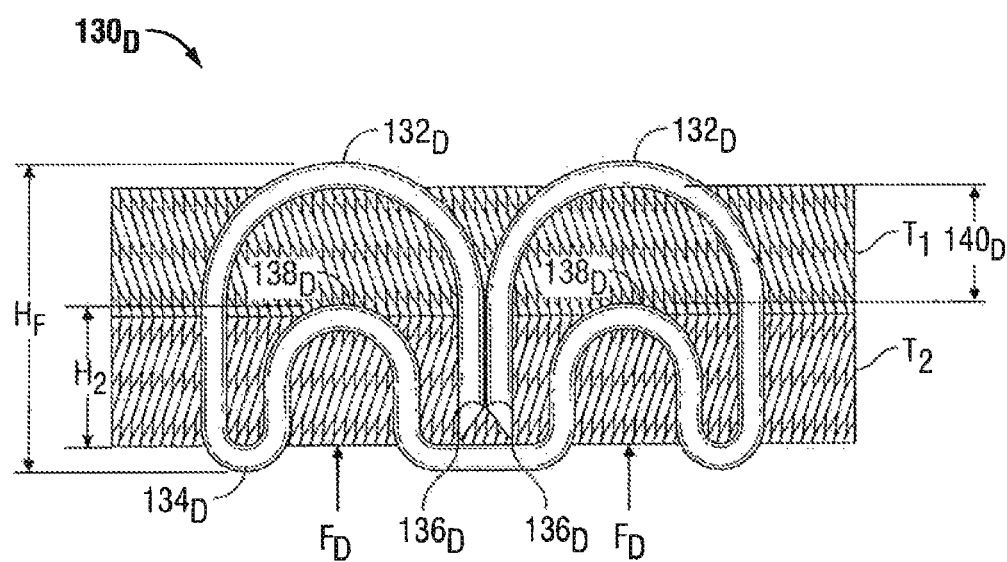
FIG. 24 is a cross-sectional view of the surgical fastener shown in FIG. 23 formed within adjacent tissue segments.

With particular reference to FIGS. 23 and 24, an alternative embodiment of the surgical fastener, identified generally by the reference character 130, is shown in its formed condition. The surgical fastener $130_D$ is similar to the surgical fastener $130_C$ discussed above with respect to FIGS. 21 and 22, in that the surgical fastener $130_D$ includes a pair of recesses/curves $138_D$ formed in the backspan $134_D$ defining a pair of humps or curves. However, the recesses/curves $138_D$ formed in the backspan $134_D$ of the surgical fastener $130_D$ define a height "$H_2$" that is greater than the height "$H_1$" of the humps or recesses $138_C$ formed in the backspan $134_C$ of the surgical fastener $130_C$ illustrated in FIGS. 21 and 22. Accordingly, when the surgical fastener $130_D$ is formed within tissue segments "$T_1$," "$T_2$," the recesses/curves $138_D$ cooperate with the legs $132_D$ of the surgical fastener $130_D$ to apply a compressive force "$F_D$" thereto. The compressive force "$F_D$" applied by the surgical fastener $130_D$ is greater than the compressive forces "F," "$F_C$" respectively applied by the surgical fasteners 130 (FIG. 2, 3), $130_C$ (FIGS. 21, 22), as the compressive space $140_D$ occupied by the tissue segments "$T_1$," "$T_2$" is less in the surgical fastener $130_D$ when compared to the compressive spaces 140 (FIG. 3), $140_C$ (FIG. 22) respectively occupied by the tissue segments "$T_1$," "$T_2$" in the surgical fasteners 130, $130_C$. Accordingly, greater pressure is applied to the tissue segments "$T_1$," "$T_2$" by the surgical fastener 130. Consequently, the flow of blood through the tissue surrounding the surgical fastener $130_D$ is more restricted when compared to the flow of blood through the tissue surrounding surgical fasteners 130 (FIG. 3), $130_C$ (FIGS. 21, 22). The dimensions of the recesses/curves $138_D$ and the compressive space $140_D$ occupied by the tissue segments "$T_1$," "$T_2$" are such that blood flow is substantially, if not completely restricted, thereby further facilitating, and effectuating hemostasis. When formed, the surgical fastener $130_D$ defines an overall height "$H_F$" that is substantially equal to those defined by the surgical fasteners 130 (FIG. 3), $130_C$ (FIG. 22).

The surgical fasteners $130_C$ (FIG. 21, 22), $130_D$ (FIGS. 23, 24) are substantially similar in configuration but for the dimensions of the hump(s) (curves) formed by the recesses $138_C$, $138_D$ formed in their respective backspans $134_C$, 134. The respective dimensions "$H_1$," "$H_2$" of the recesses/curves $138_C$, 138, as well as the dimensions of the compressive spaces $140_C$, $140_D$ occupied by tissue segments "$T_1$," "$T_2$" when the respective surgical fasteners $130_C$, $130_D$ are in their formed conditions, may be altered or varied in different embodiments to effectuate a desired level of hemostasis and blood flow in the tissue segments "$T_1$," "$T_2$" dependent upon various attributes of the tissue, e.g., thickness or the presence of scar tissue.

Figure 25:
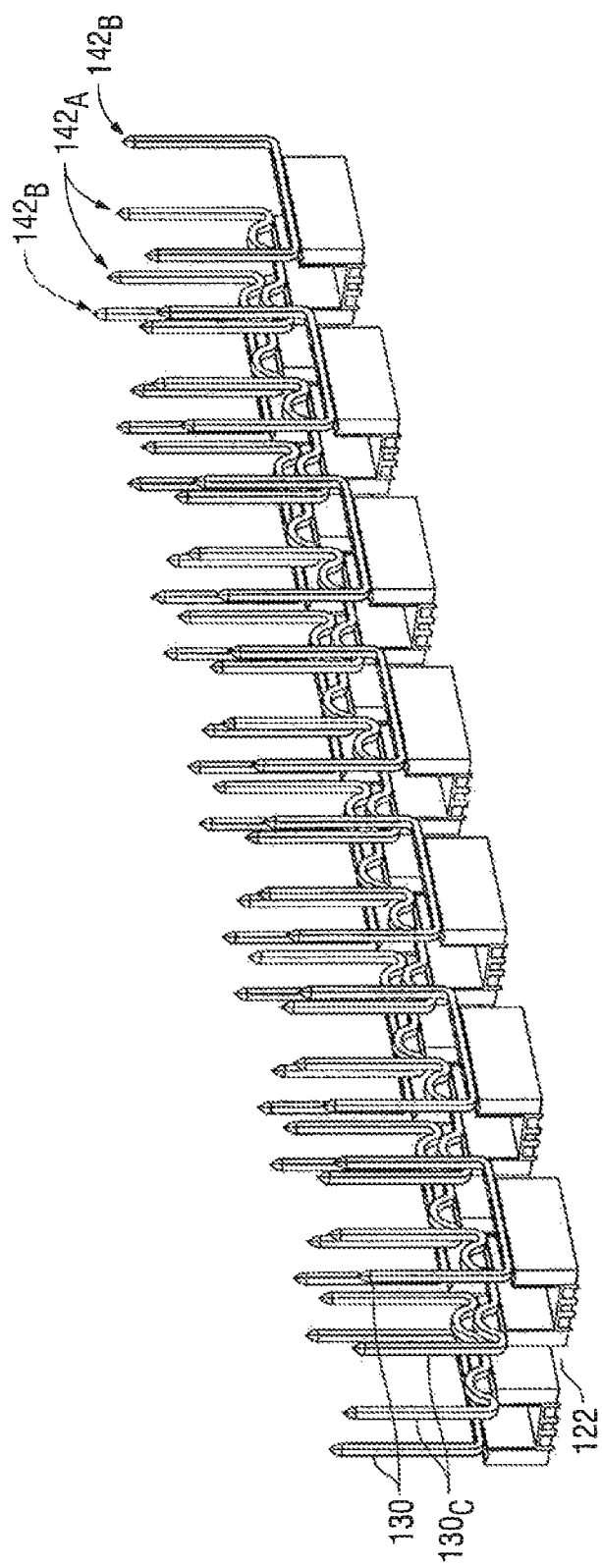
FIG. 25 is a partial longitudinal, perspective view with parts removed of the surgical fastener cartridge seen in FIG. 8 loaded with a plurality of the surgical fasteners illustrated in FIGS. 2 and 21, wherein the surgical fasteners shown in FIG. 21 are arranged in a pair of inner rows and the surgical fasteners shown in FIG. 2 are arranged in a pair of outer rows.
Figure 26:
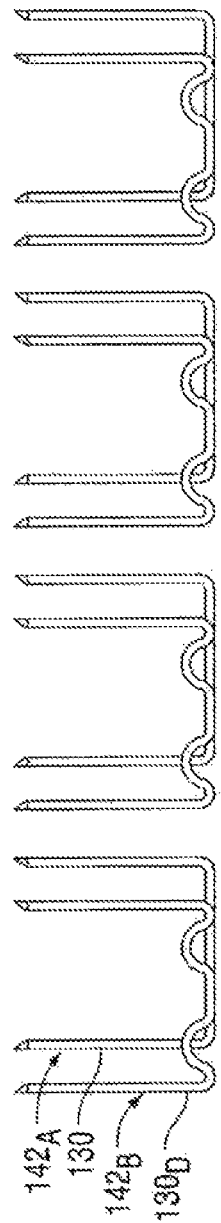
FIG. 26 is a partial longitudinal, cross-sectional view of the surgical fastener cartridge shown in FIG. 25 taken through line 10-10 in FIG. 1, which illustrates an inner and outer row of surgical fasteners.

FIGS. 25 and 26 illustrate the surgical fasteners 130 (FIG. 3) and $130_C$ (FIGS. 21, 22) installed within the cartridge body 112 seen in FIG. 1. The surgical fasteners $130_C$, 130 are arranged within the cartridge body 112 to define a pair of first (inner) rows $142_A$ and a pair of second (outer) rows $142_B$ that correspond to the respective inner and outer rows $128_A$, $128_B$ of fastener retention slots 126 formed in the top wall 120 (FIG. 1). Accordingly, the pair of inner rows $142_A$ is spaced laterally outward from the knife slot 122, on opposite sides thereof, and the pair of outer rows $142_B$ are spaced laterally outward from the pair of inner rows $14_{2A}$, again on opposite sides of the knife slot 122 and further from a central longitudinal axis of the cartridge. As such, the surgical fasteners 130, $130_C$ will be deployed on opposite sides of the cut-line (not shown) created in the tissue upon fastening. That is, the surgical fasteners $130_C$, which include the aforedescribed projections or curves $138_C$ (FIGS. 20, 21), provide a greater compressive force to the tissue, since there is a shorter distance between the projections $138_C$ and the curve of the formed legs 132, and accordingly, are provided in the inner rows $142_A$ closer to the cut-line. The fasteners 130, which define a greater distance between the curve of the legs 132 and the backspan 134 upon formation, are provided in the outer rows $142_B$, where the tissue might be thicker as a result of clamping the jaws of the apparatus, e.g. the surgical fastener applying apparatus 1000 (FIG. 1).

By positioning the fasteners providing greater tissue compression closer to the cut-line, i.e., the surgical fasteners $130_C$ in the embodiment of the surgical fastener cartridge 100 illustrated in FIGS. 24 and 25, a greater range of tissue thicknesses can be effectively sealed by a single surgical fastener cartridge. It should be appreciated however, that the present disclosure also envisions that the surgical fasteners can be positioned otherwise without departing from the scope of the present disclosure. Also, while the inner and outer rows $142_A$, $142_B$ are shown as including the surgical fasteners $130_C$, 130, respectively, the present disclosure contemplates the use of any of the surgical fasteners 130 (FIGS. 2, 3), $130_A$ (FIGS. 4, 5), $130_B$ (FIGS. 6, 7), $130_C$ (FIGS. 20, 21), $130_C$ (FIGS. 22, 23) disclosed herein above, either exclusively, such that only a single type surgical fastener, e.g., surgical fastener 130, is present in a particular row, or in combination, such that a variety of surgical fasteners, e.g., surgical fasteners 130 and $130_C$, are present.

Figure 27:
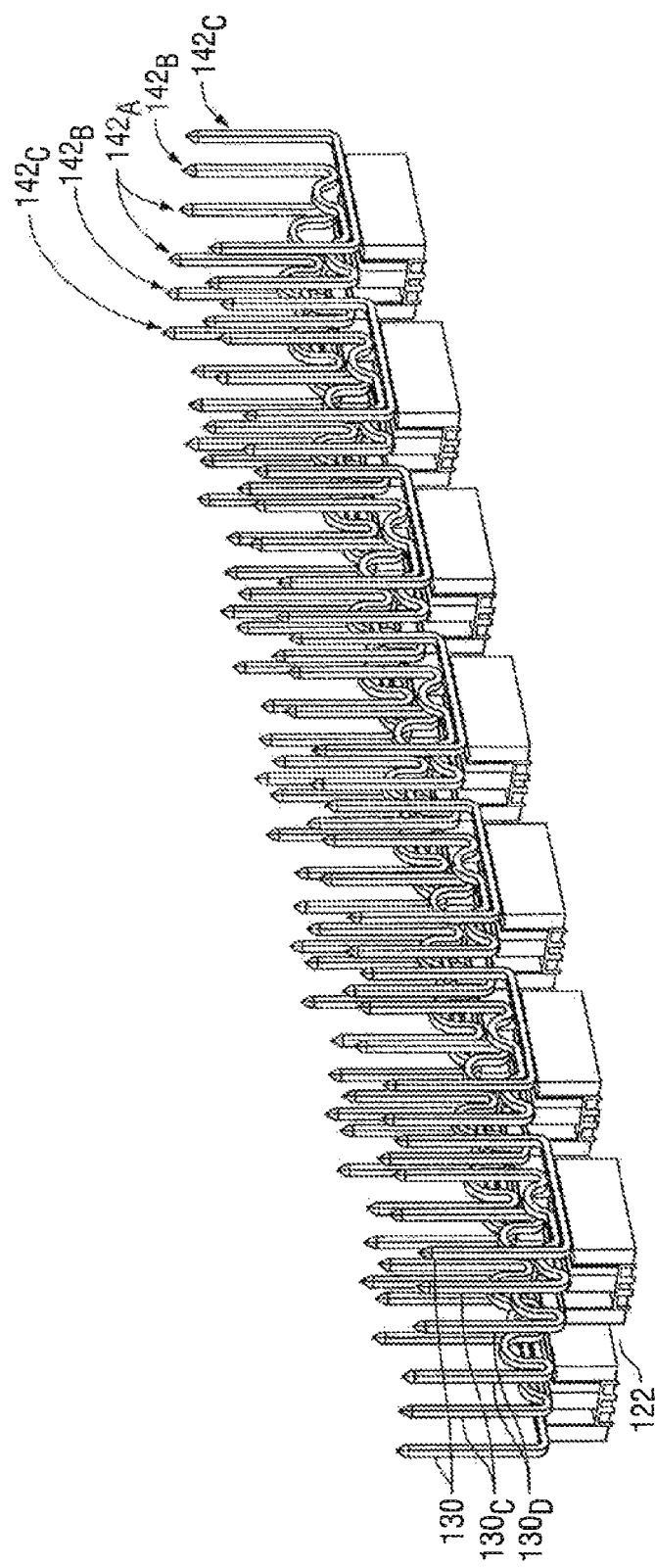
FIG. 27 is a partial top, perspective view of the surgical fastener cartridge seen in FIG. 11 when loaded with a plurality of the surgical fasteners illustrated in FIGS. 2, 21, and 23, wherein the surgical fasteners shown in FIG. 23 are arranged in a pair of inner rows, the surgical fasteners shown in FIG. 21 are arranged in a pair of intermediate rows, and the surgical fasteners shown in FIG. 2 are arranged in a pair of outer rows.
Figure 28:
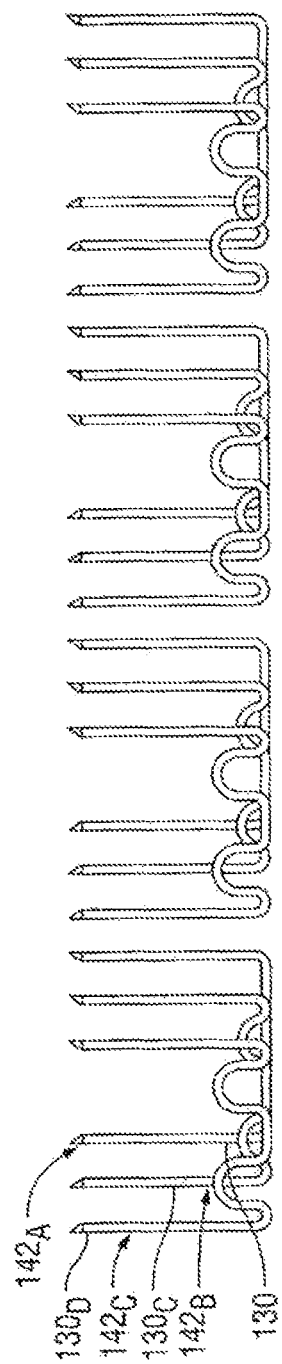
FIG. 28 is a partial longitudinal, cross-sectional view of the surgical fastener cartridge shown in FIG. 27 taken through line 14-14 in FIG. 11, which illustrates an inner, intermediate, and outer row of surgical fasteners.

FIGS. 27 and 28 illustrate another embodiment of the present disclosure in which the cartridge body 112, shown in FIG. 1, may be loaded with the surgical fasteners 130 (FIG. 3), $130_C$ (FIGS. 21, 22), and $130_D$ (FIGS. 23, 24). In this embodiment, as with the embodiment seen in FIGS. 1 and 11-14 and discussed above, the disclosed surgical fastener cartridge 100 includes a top wall 120 having a plurality of fastener retention slots 126 arranged into a pair of first (inner) rows that are spaced laterally from the knife slot 122, a pair of second (intermediate) rows that are spaced laterally from the pair of inner rows, and a pair of third (outer) rows that are spaced laterally from the pair of intermediate rows, each of which is spaced on opposite sides of the knife slot 122. Accordingly, the fasteners, e.g., surgical fasteners 130, $130_C$, $130_D$ are arranged within the cartridge body 112 to define a pair of first (inner) rows $142_A$, a pair of second (intermediate) rows $142_B$, and a pair of third (outer) rows $142_C$ that correspond to the respective inner, intermediate, and outer rows $128_A$, $128_B$, $128_C$ of fastener retention slots 126 formed in the top wall 120 of surgical fastener cartridge 100. In this embodiment, as with the embodiment of FIGS. 1 and 11-14, each of the respective inner, intermediate, and outer rows $142_A$, $142_B$, $142_C$ may comprise any of the surgical fasteners 130, $130_C$, $130_D$ disclosed herein, either exclusively, such that only a single type surgical fastener, e.g., surgical fastener 130, is present in a particular row, or in combination, such that a variety of surgical fasteners, e.g., surgical fasteners 130, $130_C$, and $130_D$, are present. In the particular embodiment shown in FIGS. 27 and 28, however, the respective outer, intermediate, and inner rows $142_C$, $142_B$, and $142_A$ are comprised solely of the surgical fasteners 130, $130_C$, $130_B$, such that the flow of blood through the tissue immediately surrounding the cut-line is more restricted by the inner row $142_A$ of surgical fasteners 130, whereas the flow of blood through the tissue surrounding the respective intermediate and outer rows $142_B$, $142_C$, respectively, is less restricted by the surgical fasteners $130_C$, 130, respectively. Accordingly, the flow of blood will be minimized in the tissue immediately adjacent the cut-line, and will be increased gradually with the lateral distance from the cut-line. Also, by this arrangement, the surgical fasteners with the largest curved portions/recesses, e.g., the surgical fasteners 130, will be positioned closest to the cut-line where the tissue is generally compressed to a greater extent, and the surgical fasteners providing for less compression, e.g., the surgical fasteners 130, which include a substantially linear backspan 134, as described above, will be positioned further from the cut-line where the tissue is generally compressed to a lesser extent.

The above description, disclosure, and figures should not be construed as limiting, but merely as exemplary of particular embodiments. It is to be understood, therefore, that the disclosure is not limited to the precise embodiments described, and that various other changes and modifications may be effected by one skilled in the art without departing from the scope or spirit of the disclosure. Additionally, those skilled in the art will appreciate that the elements and features illustrated or described in connection with one embodiment can be combined with those of another, and that such modifications and variations are also intended to be included within the scope of the present disclosure.

The invention claimed is:

1. A tool assembly for use with a surgical fastener applying apparatus, the tool assembly comprising:
   a first jaw including a cartridge assembly having a plurality of surgical fasteners disposed within the cartridge assembly, each surgical fastener in the plurality of surgical fasteners including a pair of legs terminating in penetrating ends, and a backspan connecting the pair of legs, the backspan defining a longitudinal axis and having a twisted configuration such that a face of the backspan is rotated along a length of the backspan around the longitudinal axis, creating a spiral backspan configuration.

2. The tool assembly of claim 1, wherein the cartridge assembly includes a plurality of first surgical fasteners disposed within the cartridge assembly, and a plurality of second surgical fasteners disposed within the cartridge assembly, each of the plurality of first surgical fasteners including a first backspan defining a first longitudinal axis and having a twisted configuration such that a face of the first backspan is rotated along at least a portion of the length of the first backspan about the first longitudinal axis, and each of the plurality of second surgical fasteners including a second backspan defining a second longitudinal axis and having a twisted configuration such that a face of the second backspan is rotated along at least a portion of the length of the second backspan about the second longitudinal axis, dimensions of the first backspan being different than dimensions of the second backspan.

3. The tool assembly of claim 2, wherein the first backspan defines a first height, and the second backspan defines a second height different than the first height such that the plurality of first surgical fasteners apply a first compressive force to tissue upon formation, and the plurality of second surgical fasteners apply a second, different compressive force to tissue upon formation.

4. The tool assembly of claim 2, wherein the plurality of first surgical fasteners and the plurality of second surgical fasteners are dimensioned such that the second height is greater than the first height, whereby the second compressive force is greater than the first compressive force.

5. The tool assembly of claim 4, wherein the plurality of first surgical fasteners are arranged in a first row, and the plurality of second surgical fasteners are arranged in a second row spaced apart from the first row.

6. The tool assembly of claim 5, wherein the cartridge assembly includes a channel configured to accommodate a cutting member for the creation of a cut-line in the tissue.

7. The tool assembly of claim 6, wherein the first row of surgical fasteners is positioned a first distance from the channel, and the second row is positioned a second, greater distance from the channel.

8. The tool assembly of claim 7, further comprising a plurality of third surgical fasteners, each of the surgical fasteners in the plurality of third surgical fasteners including a third backspan defining a third longitudinal axis and having a twisted configuration such that a face of the third backspan is rotated along a length of the third backspan about the third longitudinal axis, the dimensions of the third backspan being different than the dimensions of at least one of the first backspan and the second backspan.

9. The tool assembly of claim 8, wherein the third backspan defines a third height different than at least one of the first height and the second height such that the plurality of third surgical fasteners apply a third compressive force to tissue upon formation different than at least one of the first compressive force and the second compressive force.

10. The tool assembly of claim 9, wherein the plurality of third surgical fasteners define an overall height when formed that is equal to the overall height defined by the plurality of first surgical fasteners and the plurality of second surgical fasteners when formed.

11. The tool assembly of claim 10, wherein the plurality of third surgical fasteners are dimensioned such that the third height is greater than the second height, whereby the third compressive force is greater than the second compressive force.

12. The tool assembly of claim 1, wherein the backspan includes multiple twists such that at least two portions of the backspan extend in a same direction as the penetrating ends of the legs.

13. A surgical fastener for use in a medical procedure, the surgical fastener including a pair of legs terminating in penetrating ends configured to pass through tissue, and a backspan connecting the pair of legs defining a longitudinal axis and having a twisted configuration, such that a face of the backspan is rotated along a length of the backspan around the longitudinal axis, creating a spiral backspan configuration, such that the backspan defines a non-uniform tissue contacting surface.

14. A surgical fastener applying apparatus comprising:
a handle portion;
an elongate body portion extending distally from the handle portion; and
a tool assembly supported adjacent a distal end of the elongate body portion, the tool assembly including:
a first jaw including an anvil assembly; and
a second jaw pivotally coupled to the first jaw such that the tool assembly is repositionable to clamp tissue between the first jaw and the second jaw, the second jaw including a cartridge assembly having a plurality of surgical fasteners disposed within the cartridge assembly, each surgical fastener in the plurality of surgical fasteners including a pair of legs terminating in penetrating ends, and a backspan connecting the pair of legs having a twisted configuration, such that a face of the backspan is rotated along a length of the backspan around a longitudinal axis of the backspan, creating a spiral backspan configuration, such that the backspan defines a non-linear tissue contacting surface.

15. The surgical fastener applying apparatus of claim 14, wherein the backspan of each surgical fastener in the plurality of surgical fasteners includes multiple twists such that at least two portions of the backspan extend in a same direction as the penetrating ends of the legs.

16. The surgical fastener applying apparatus of claim 14, wherein the cartridge assembly includes a plurality of first surgical fasteners disposed therein, and a plurality of second surgical fasteners disposed therein, each of the surgical fasteners in the plurality of first surgical fasteners including a first backspan having a first face oriented in different directions along a length of the first backspan such that the first backspan defines a first non-linear tissue contacting surface, and each of the surgical fasteners in the plurality of second surgical fasteners including a second backspan having a second face oriented in different directions along a length of the second backspan such that the second backspan defines a second non-linear tissue contacting surface, the dimensions of the first backspan being different than the dimensions of the second backspan.

17. The surgical fastener applying apparatus of claim 16, wherein the first backspan defines a first height, and the second backspan defines a second height different than the first height such that the plurality of first surgical fasteners apply a first compressive force to tissue upon formation, and the plurality of second surgical fasteners apply a second, different compressive force to tissue upon formation.

* * * * *